United States Patent [19]
Kawada et al.

[11] Patent Number: 5,916,578
[45] Date of Patent: Jun. 29, 1999

[54] LIPID COMPOSITION CONTAINING A LIQUID CRYSTAL PHASE

[75] Inventors: Izumi Kawada; Kazutoshi Sakurai; Kazuhiko Tokoro, all of Kanagawa, Japan

[73] Assignee: Takasago International Corporation, Tokyo, Japan

[21] Appl. No.: 08/928,643

[22] Filed: Sep. 12, 1997

[30] Foreign Application Priority Data

May 2, 1997 [EP] European Pat. Off. .............. 97400997

[51] Int. Cl.⁶ .......................... A61K 7/00; A61K 31/045
[52] U.S. Cl. ....................... 424/401; 424/70.1; 514/844; 514/847; 514/880; 514/724; 514/727
[58] Field of Search ..................................... 424/401, 701, 424/DIG. 1, 59–64; 514/844–848, 880, 881, 724, 727

[56] References Cited

U.S. PATENT DOCUMENTS 5,531,925  7/1996  Landh ................. 252/299.01

*Primary Examiner*—Gollamudi S. Kishore
*Attorney, Agent, or Firm*—Sughrue, Mion, Zinn, Macpeak & Seas, PLLC

[57] ABSTRACT

A composition comprising a 2-acetaminoalkane-1,3-diol or its optical isomer having the formula:

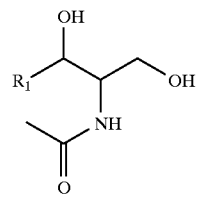

wherein $R_1$ represents a linear alkyl group having 9 to 17 carbon atoms; a 2-acylaminoalkane-1,3-diol or its optical isomer having the formula:

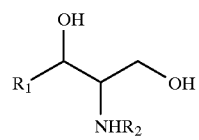

wherein $R_1$ has the same meaning as given above for formula (I) and $R_2$ represents a substituted or unsubstituted linear acyl group having 14 to 24 carbon atoms; and a compound having a sterol group. This composition forms a lamellar liquid crystal phase and can retain moisture when applied to the skin.

39 Claims, 12 Drawing Sheets

LIPID COMPOSITION CONTAINING A LIQUID CRYSTAL PHASE

BACKGROUND OF THE INVENTION

1. Field of the Invention

The present invention relates to a novel composition containing a liquid crystal phase, and in particular, to a lipid composition comprising a mixture of compounds belonging to the ceramide family and a medium suited for cosmetic or pharmaceutical use.

The lipid composition according to the invention may comprise a racemic 2-acetaminoalkane-1,3-diol, i.e., N-acetylsphinganine, or an optically active form thereof; a racemic 2-acylaminoalkane-1,3-diol or an optically active form thereof; and cholesterol, and optionally a cholesterol ester, e.g., cholesteryl hydroxystearate; iso-stearic acid; and/ or other higher fatty acids.

The composition may further comprise a triglyceride, a phospholipid or other cosmetically or pharmaceutically acceptable vehicles or excipients. Such a composition may especially be appropriate for use as a cosmetic product, an externally applicable skin preserver, a bath additive, a hair-care product, or the like.

The composition described above is capable of retaining moisture on the subject to which it is applied. When it is applied on the skin, it renders skin humid and fair, and reactivates skin cells. The composition thus protects the skin and provides a suitable cosmetic, dermatological or bath-additive product. When applied to the scalp or hair, subsequent hair-washing does not cause a loss of water-soluble proteins or amino acids from hair so that it is protected from drying-out.

To render the skin moist and smooth, the water content retained in the stratum corneum (horny layer) of the skin plays an important role. Water seems to be retained in this stratum corneum by free amino acids, organic acids, urea, inorganic ions or the like, contained therein. Such substances are actually used alone or in combination for preparing a dermatological cosmetic product or medicine for external application, in order to prevent or cure rough skin.

2. Description of the Prior Art

It has been found only recently that intercellular lipids contained in the stratum corneum have a high water-retaining capacity and usually contain about 30% water. These lipids control the evaporation of corporal water and prevent external stimulants from penetrating, to thereby preserve the tenderness and smoothness of the skin.

Among the intercellular lipid components, a ceramide in particular, but also a cholesterol ester, are known to improve rough skin when applied thereto. Especially, the ceramide serves as an efficient barrier to water migration.

The intercellular lipids consist mainly of ceramides, cholesteryl sodium sulphate, palmitic acid and cholesterol. In view of the above, a composition containing these same components, in which the ceramide corresponds to a racemate having the formula (II), was prepared and described in Japanese Unexamined Patent Application No. Hei 4-327563.

Conversely, it was found that the level of ceramide content in a patient suffering from rough or dry skin, or atopic dermatitis is considerably low, as compared with the skin of a healthy person.

Ceramides were also isolated and identified by G. Hussler et al. from lipids contained in human hair (*Int. J. Cosmet. Sci.,* 17, 197, 1995). These ceramides have a high capacity for retaining water. A racemic ceramide was then synthesized and incorporated into a lipid composition for hair-washing. It was proposed that the lipid composition reduces the loss of proteins and amino acids from hair when it is washed to protect and prevent the hair from drying-out (European Patent 0 278 505).

It was also reported by M. Philippe et al. that a composition containing a synthesized racemic ceramide reduces the water loss of hair (*Int. J. Cosmet. Sci.,* 17, 133, 1995).

Under these circumstances, research is currently being carried out into the application of ceramide-containing, intercellular lipid-type substances to rough skin, in view of improving the state of the skin.

Ceramides are scarcely soluble in water or any organic solvent. To provide ceramides in the skin, it is thus necessary to first prepare a lipid composition having a specific mixture ratio so as to form a lamellar liquid crystal structure, and to put this intact structure into a cosmetically or pharmaceutically usable form. The lamellar liquid crystal structure can be formed by adding a fatty acid or cholesterol to the ceramide. The ceramides can be dissolved in a fatty acid, and then incorporated into the lamellar liquid crystal structure. For the above purpose, a surfactant is usually added to promote penetration of the lamellar liquid crystal structure into the skin, but crystals other than the ceramides should not be added thereto. Moreover, a specific sort of surfactant must be selected in order to promote the penetration of intercellular lipids into the stratum corneum and also to promote the formation of a lamellar liquid crystal. The intercellular lipids consist mainly of a ceramide, cholesterol, a fatty acid such as palmitic acid and cholesterol sulphate. A mixture of these components usually forms a lamellar liquid crystal structure. This structure can also be formed in the absence of the fatty acid or cholesterol sulphate. However, according to the report by P. W. Wertz et al., the ceramide alone, or together with cholesterol, does not form a homogeneous lamellar liquid crystal structure (*J. Invest. Dermatol.,* 87, 582, 1986).

On the other hand, a hair-protecting composition has been proposed consisting of a ceramide or glucoceramide, a cholesterol ester and a cosmetically acceptable vehicle (Japanese Unexamined Patent Application No. Sho 63-270617). The ceramide or the glucoceramide, e.g., cerebroside, used in this composition is extracted from a material of animal origin such as pig skin, bovine brain and red corpuscles (haematid), or from a plant. Among these possibilities, bovine brain extract is considered to be the most appropriate product. However, since the eruption of bovine spongiform encephalitis (mad cow disease), this product may no longer be used.

A hair-protecting composition has also been proposed containing either a ceramide or glycoceramide and at least one kind of cholesterol ester (Japanese Patent No. 2,510, 235).

In another study, a lipid component was selected from the group consisting of a ceramide, a pseudoceramide, a polyester consisting of a polyol and a fatty acid, a phospholipid, a galactosyldiacylglycerol, a sphingoglycolipid, a derivative of succinic acid and a mixture thereof and incorporated into a lipid lamella, in order to cure xeroderma (Japanese Unexamined Patent Application No. Hei 6-157283).

Furthermore, a composition has been provided for use as a bath additive containing a ceramide and a compound having a pseudo-ceramide structure (Japanese Unexamined Patent Application No. Hei 8-34726).

Still further, a mixture was prepared containing a complex product or composition having a liquid crystal phase, an amphoteric and/or semi-polar surfactant, a higher fatty acid and water. Use of the mixture allows cosmetic make-up to hold properly and longer, and to more efficiently resist the deteriorating effect of water and cutaneous fat (Japanese Unexamined Patent Application No. Hei 8-217633).

SUMMARY OF THE INVENTION

It is therefore an object of the present invention to provide a composition which enhances the moisture-retaining capacity of the stratum corneum and cures or treats rough skin.

Another object of the invention is to provide a cosmetic or pharmaceutical product comprising this composition. The product cares for and protects the skin. It can be used as an externally applicable skin-care product.

Due to its moisture-retaining capacity, the composition also protects the hair from drying-out and splitting. Therefore, a further object of the invention is to provide a hair-care product.

Still another object is to provide a composition or a product for use as a bath additive.

To this end, the invention provides a composition comprising:
at least a component A selected from the group consisting of 2-acetaminoalkane-1,3-diols having the formula (I) and optically active forms thereof:

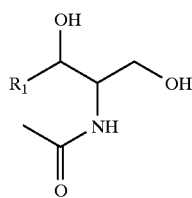

(I)

wherein $R_1$ represents a linear alkyl group having from 9 to 17 carbon atoms;
at least a component B selected from the group consisting of 2-acylaminoalkane1,3-diols having the formula (II) and optically active forms thereof:

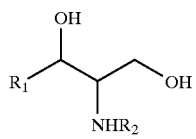

(II)

wherein $R_1$ has the same meaning as given above for formula (I) and $R_2$ represents a linear acyl group having from 14 to 24 carbon atoms; and
at least a component C having a sterol group, said components A, B and C being mixed in such proportion so as to form a liquid crystal phase. Component C may be cholesterol.

The linear acyl group represented by $R_2$ in formula (II) may be substituted or unsubstituted, and may also contain a carbon-carbon double bond. Examples of the substituents for the substituted linear acyl group represented by $R_2$ include methyl group (for example, geranoyl) and hydroxy group (for example, ricinoyl). Examples of the linear acyl group containing a carbon-carbon double bond represented by $R_2$ include oleoyl group ((z)-9-octadecenoyl), linoleoyl group ((z,z)-9,12-octadecadienoyl) and linolenoyl group (9,12,15-octadecatrienoyl).

Preferably, the components A and B are mixed in a weight proportion ranging from 1:1 to 1:8.

In a preferred embodiment, the component A is a (2S, 3R)-2-acetaminoalkane-1,3-diol having the formula (III):

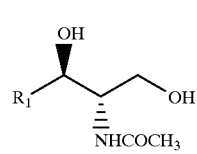

(III)

wherein $R_1$ represents a linear alkyl group having from 9 to 17 carbon atoms.

Likewise, the component B is preferably a (2S,3R)-2-acylaminoalkane-1,3-diol having the formula (IV):

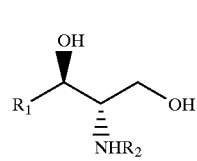

(IV)

wherein $R_1$ has the same meaning as given above for formula (I) and $R_2$ represents a linear acyl group having from 14 to 24 carbon atoms.

The linear acyl group represented by $R_2$ in formula (IV) may be substituted or unsubstituted, and may also contain a carbon-carbon double bond.

$R_2$ in component B preferably is an acyl group having a hydroxy group on the 2-carbon position or an oleoyl group.

When $R_2$ is an oleoyl group, the weight proportion of components A to B ranges from 1:1 to 1:8, the weight proportion of components B to C ranges from 7:1 to 1:3 and preferably from 7:1 to 1:1, and the weight proportion of components A to C ranges from 2:1 to 1:7 and preferably from 1:1 to 1:3.

The composition according to the invention may further comprise a component D selected from the group consisting of a cholesterol derivative, a fatty acid and a derivative of a fatty acid.

The derivative of cholesterol as component D may be cholesteryl hydroxystearate.

Then, preferably the total of the components A and B, and the cholesterol as component C are mixed in a weight proportion ranging from 5:4 to 5:1, whereas the component C and the cholesteryl hydroxystearate as component D, are mixed in a weight proportion ranging from 4:1 to 1:5.

Alternatively, the fatty acid or a derivative thereof as component D may be isostearic acid or cholesteryl hydroxystearate.

In the case of isostearic acid, the total of the components A and B, and the cholesterol as component C are mixed in a weight proportion ranging from 5:1 to 2:1 and preferably from 5:1 to 3:1, whereas the component C and the isostearic acid as component D are mixed in a weight proportion ranging from 1:1 to 1:4.

The composition according to the invention may further comprise at least one compound selected from the group consisting of a triglyceride and a phospholipid.

The invention also provides a cosmetic product comprising the composition defined above and a cosmetically acceptable medium.

The cosmetic product thus obtained may be used as a skin-protecting agent, an agent for adding to a bath, a hair-protecting agent, or the like.

The invention further provides a pharmaceutical product comprising the composition defined above and a pharmaceutically acceptable medium.

The composition may be used in the manufacture of a medicine for protecting the skin in combination with a pharmaceutically acceptable medium.

To form a lamellar liquid crystal structure, the composition of the invention may be homogeneously mixed, heated above its melting temperature and then gradually cooled.

The composition may also be homogeneously mixed, supplemented with water and repeatedly frozen and thawed, so as to increase its hydration level.

Furthermore, the composition may be homogeneously mixed, dissolved in a solvent and supplemented with water, to precipitate a liquid crystal phase.

Moreover, the liquid crystal phase can also be formed by other methods known in the art.

The composition according to the invention includes all products containing the liquid crystal phase, and is not limited to products prepared using the above liquid-crystal forming methods.

BRIEF DESCRIPTION OF THE DRAWINGS

The above and other objects, features and advantages of the invention will become apparent from the following description of the preferred embodiments, given as nonlimiting examples, with reference to the accompanying drawings, in which.

DETAILED DESCRIPTION OF THE PREFERRED EMBODIMENTS

The 2-acetaminoalkane-1,3-diol and 2-acylaminoalkane-1,3-diol for use in the present invention may be prepared by a chemical synthesis. These compounds can either be a racemic substance, a natural-type optical isomer or a non-natural-type optical isomer, or further still a combination thereof.

In 2-acetaminoalkane-1,3-diol where $R_1$ represents a linear alkyl group having 11 to 17 carbon atoms, $R_1$ may typically have 15 carbon atoms. Then, the product may either be a racemate of 2-acetaminooctadecane-1,3-diol, a natural optical isomer (2S,3R)-2-acetaminooctadecane-1,3-diol, a non-natural optical isomer (2S,3S)-, (2R,3R)- or (2R,3S)-2-acetaminooctadecane-1,3-diol, or a mixture thereof. However, the 2-acetaminooctadecane-1,3-diols for use in the invention are not limited to the above-mentioned products and extend to substances having various carbon numbers and configurations as defined in the invention.

The racemate can be prepared by acetylating commercially available 2-aminooctadecane-1,3-diol. It can also be obtained according to the method described by D. Shapiro et al., in *J. Am. Chem. Soc.*, 80, 2170, 1958.

As shown below, the ester and ketone groups in an ester of 2-acetamino-3-oxooctadecanoic acid are reduced in the presence of lithium aluminium hydride (referred to as LAH) to obtain a racemate of 2-acetaminooctadecane-1,3-diol, as follows:

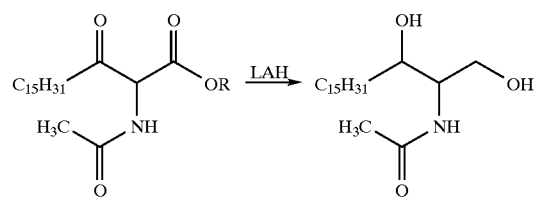

Although this racemate can form a liquid crystal necessary for the purpose of the present invention, it crystallizes rather rapidly and the crystals thus formed are not sufficiently stable. For this reason, the racemate has a lower moisture-retaining capacity than its corresponding optically active isomers.

In order to obtain optically active isomers of the component A(I), an ester of 2-acetamino-3-oxoalkanoic acid is prepared beforehand according to the method of D. Shapiro described in *J. Am. Chem. Soc.*, 80, 2170, 1958, as follows:

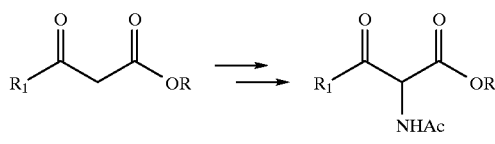

$R_1 = C_{15}H_{31}$
$R; C_1 \sim C_4\text{-alkyl}$

This product is asymmetrically hydrogenized in the presence of a complex of ruthenium and optically active phosphine, e.g., (−)-phosphine, to obtain the ester of (2R, 3S)-2-acetamino-3-hydroxyalkanoic acid, for example, as described in Japanese Unexamined Patent Application No. Hei 6-80617.

Figure 1:
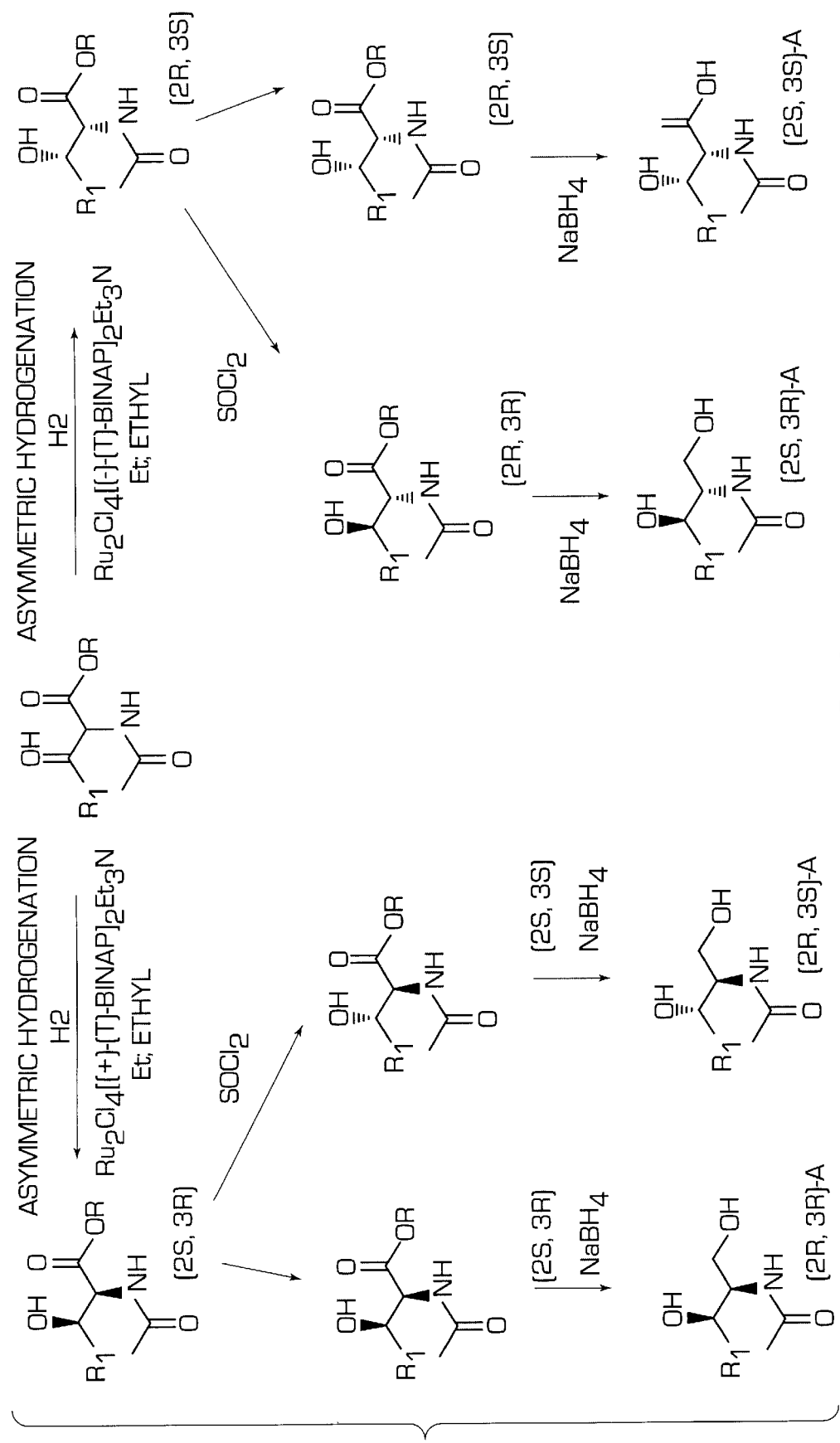
FIG. 1 shows the reaction scheme for preparing optically active 2-acetaminoalkane-1,3-diols from an ester of 2-acetamino-3-oxoalkanoic acid.

The latter product is then allowed to react with thionylchloride to invert the steric configuration of the hydroxy group and to obtain the ester of (2R,3R)-2-acetamino-3-hydroxyalkanoic acid. The ester group is subsequently reduced in the presence of sodium borohydride to obtain the desired (2S,3R)-2-acetaminoalkane-1,3-diol. If the hydroxy group is not sterically inverted, a (2S,3S)-type substance is obtained. Furthermore, if (+)-phosphine is used in the ruthenium-phosphine complex instead of (−)-type, (2R,3R)- and (2R,3S)-types are obtained. This process is summarized in FIG. 1.

Typical examples of component A represented formula (I) include a racemic or optically active substance comprising an aminodiol derivative such as 2-acetaminododecane-1,3-diol, 2-acetaminotridecane-1,3-diol, 2-acetaminotetradecane-1,3-diol, 2-acetaminopentadecane-1,3-diol, 2-acetaminohexadecane-1,3-diol, 2-acetaminoheptadecane-1,3-diol, 2-acetaminooctadecane-1,3-diol, 2-acetaminononadecane-1,3-diol, 2-acetaminoeicosane-1,3-diol, or the like.

The component B represented by formula (II) of the present invention may be obtained by de-acetylating the corresponding racemic or optically active component A(I) to obtain the corresponding 2-aminoalkane-1,3-diol (dihydrosphingosine), and then by acylating the latter with an appropriate acylating agent as follows:

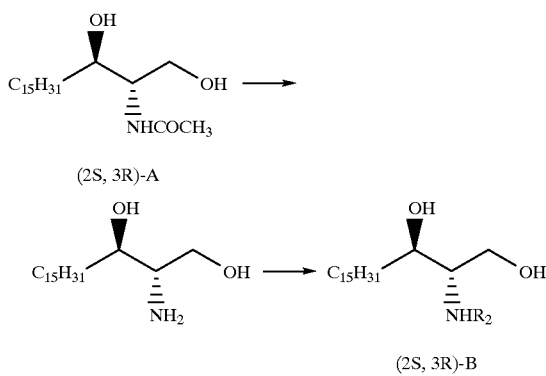

The acylating agent may include, for example, a commercially available higher fatty acid and a derivative thereof such as a fatty acid halide, a fatty acid anhydride, anhydrides of mixed fatty acids, a fatty acid ester, a p-nitrophenyl ester of a fatty acid, an N-hydroxysuccinimide ester of a fatty acid, or the like.

Typically, the acylating agent may be tetradecanoic acid, pentadecanoic acid, hexadecanoic acid, heptadecanoic acid, octadecanoic acid, nonadecanoic acid, eiconsanoic acid, or a chloride, anhydride or N-hydroxysuccinimide of these (single or mixed) fatty acids, or a lower alkyl or p-nitrophenyl ester prepared therefrom.

Typical examples of component B include a racemic or optically active substance comprising 2-tetradecanoylaminooctadecane-1,3-diol, 2-pentadecanoylaminooctadecane-1,3-diol, 2-hexadecanoylaminooctadecane-1,3-diol, 2-heptadecanoylaminooctadecane-1,3-diol, 2-octadecanoylaminooctadecane-1,3-diol, 2-nonadecanoylaminooctadecane-1,3-diol, 2-eicosanoylaminooctadecane-1,3-diol, 2-heneicosanoylaminooctadecane-1,3-diol, 2-docosanoylaminooctadecane-1,3-diol, 2-tricosanoylaminooctadecane-1,3-diol, or 2-tetracosanoylaminooctadecane-1,3-diol.

When $R_2$ in component B is an acyl group having a hydroxy group on the 2-carbon position, the acylating agent may be a commercially available higher fatty acid having a hydroxy group protected by a group such as an acetyl group. The acylating agent may contain a halide or N-hydroxysuccinimide of a single or mixed higher fatty acid or a lower alkyl or p-nitrophenyl ester prepared therefrom. It is also possible to use, as an acylating agent, an ester of a higher fatty acid in which the hydroxy group is not protected.

Typical examples of the acylating agent include 2-hydroxytri-, tetra-, penta-, hexa-, hepta-, octa-, or nona-decanoic acid, 2-hydroxyeicosanoic acid, 2-hydroxydocosanoic acid, 2-hydroxytricosanoic acid, 2-hydroxytetracosanoic acid, or an acetylated form selected from a chloride, anhydride, mixed anhydride, p-nitrophenyl ester, N-hydroxysuccinimide and a lower-carbon ester thereof. When 2-hydroxy fatty acid is esterified with an alkyl group having from 1 to 4 carbon atoms, acylation may be carried out without the hydroxy group being protected by an acetyl group. The resulting product is then a corresponding racemic or optically active 2-hydroxy derivative such as (2S,3R)-2-(2-hydroxytetra-, penta-, hexa-, hepta-, octa-, nona-decanoyl- or eicosanoyl-, docosanoyl-, tricosanoyl-, or tetracosanoyl-amino)octadecane-1,3-diol, etc.

When $R_2$ in the component B is a 2-oleoyl group, the acylating agent may either be a commercially available, high purity cis-9-octadecenoic acid (oleic acid of 99% or 91% purity by weight, produced by NOF Corporation) or a commercially available cis-9-octadecenoic acid reagent (oleic acid having a purity of 75 to 85% by weight, produced by NOF Corporation, Nacarai Tesque, Tokyo Kasei, etc.). It may also be cis-9-octadecenoyl chloride, cis-9-octadecenoyl p-nitrophenyl, cis-9-octadecenoyl N-hydroxysuccinimide, a lower alkyl ester of cis-9-octadecenoic acid, etc., prepared therefrom.

When high-purity cis-9-octadecenoic acid is used, the resultant product is mainly a corresponding racemic or optically active derivative such as (2S,3R)-2-(cis-9-octadecenoylamino)dodecane-, tridecane-, tetradecane-, pentadecane-, hexadecane-, heptadecane-, octadecane-, nonadecane-, or eicosane-1,3-diol, etc.

The commercial cis-9-octadecenoic acid reagent (oleic acid) has a purity of about, or a little higher than, 70% by weight, and contains impurities such as tetradecanoic acid, hexadecanoic acid, cis-9-hexadecenoic acid, octadecanoic acid, cis, cis-9, 12-octadecadienoic acid, etc., or a derivative thereof.

Accordingly, when this commercial reagent or its derivative is used to synthesize 2-cis-9-octadecenoylaminoalkane-1,3-diol, the resultant product contains not only (2S,3R)-2cis-9-octadecenoylaminoalkane-1,3-diol as a main product, but also dihydroceramides as by-products, which are formed by the amide-bonding of the impurities with 2-aminoalkane-1,3-diol. These by-products include (2S,3R)-2-tetradecanoylaminoalkane-1,3-diol, (2S,3R)-2-hexadecanoylaminoalkane-1,3-diol, (2S,3R)-2-octadecanoylaminoalkane-1,3-diol, (2S,3R)-2-(cis-9-hexadecenoylamino)alkane-1,3-diol, (2S,3R)-2-octadecanoylaminoalkane-1,3-diol, (2S,3R)-2-(cis,cis-9,12-octadecadienoylamino)alkane-1,3-diol, etc. A mixture of these cis-9-octadecenoic acid-derived products having 14 to 18 saturated or unsaturated carbon atoms are collectively called (2S,3R)-2-oleoylaminoalkane-1,3-diols.

The sterol (component C) for use in the invention is preferably cholesterol. The cholesterol may be of animal- or plant-origin. It may also be a commercially available synthetic cholesterol having a high purity such as the one produced by Nacarai Tesque. Examples of component C having a sterol group other than cholesterol for use in this invention include coprostanol, stigmasterol, β-sitosterol and ergosterol.

The fatty acid for use in the invention may be tetradecanoic acid (myristic acid), hexadecanoic acid (palmitic acid), octadecanoic acid (stearic acid), hydroxyoctadecanoic acid (hydroxystearic acid), isostearic acid or the like. Among them, isostearic acid is preferred. The fatty acid having a higher carbon content may be a commercially available product. Isostearic acid for use in the invention may be a commercially available 2-(1,3,3-trimethylbutyl)-5,7,7-trimethyloctanoic acid.

To form a liquid crystal structure, the appropriate proportion of component A, component B, cholesterol (component C) and optionally an additive to be mixed may vary depending on the kind and purity of the components A, B and C and the additive that is used. However, a suitable proportion can be readily determined. Usually, 2-acetaminoalkane-1,3-diol (component A) plays an important role in forming a lamellar liquid crystal. Without component A, it can be difficult to form a stable lamellar liquid crystal structure.

When three components, i.e., a (2S,3R)-2-acetaminoalkane-1,3-diol (A), a (2S,3R)-2-oleoylaminoalkane-1,3-diol (B) and cholesterol (C) are used, the weight proportions of A to B, B to C and A to C range from 1:1 to 1:8, from 7:1 to 1:3 and from 2:1 to 1:7, respectively.

More specifically, when (2S,3R)-2-acetaminooctadecane-1,3-diol (A), (2S,3R)-2-oleoylaminooctadecane-1,3-diol (B) and cholesterol (C) are used, the weight proportions of A to B and B to C preferably range from 1:1 to 1:8 and from 7:1 to 1:1, respectively.

When (2S,3R)-2-acetaminooctadecane-1,3-diol (A), (2S,3R)-2-oleoylaminohexadecane-1,3-diol (B) and cholesterol (C) are used, the weight proportions of A to B and B to C preferably range from 1:6 to 1:3 and from 6:1 to 3:2, respectively.

When (2S,3R)-2-acetaminohexadecane-1,3-diol (A), (2S,3R)-2-oleoylaminooctadecane-1,3-diol (B) and cholesterol (C) are used, the weight proportions of A to B and B to C preferably range from 1:5 to 2:5 and 5:1 to 1:1, respectively.

When (2S,3R)-2-acetaminohexadecane-1,3-diol (A), (2S,3R)-2-oleoylhexadecane-1,3-diol (B) and cholesterol (C) are mixed, the weight proportions of A to B and B to C preferably range from 1:4 to 1:1 and from 3:1 to 1:1, respectively.

When (2S,3R)-2-acetaminotetradecane-1,3-diol (A), (2S,3R)-2-oleoylaminooctadecane-1,3-diol (B) and cholesterol (C) are mixed, the weight proportions of A to B and B to C preferably range from 1:1 to 1:4 and from 2:1 to 1:1, respectively.

The optional additive according to the invention may be a cholesterol ester. Typical examples of the cholesterol ester are cholesteryl oleate, cholesteryl stearate, cholesteryl hydroxystearate, cholesteryl isostearate, or the like. These products can be synthesized chemically and are commercially available as high purity products. Among them, cholesteryl hydroxystearate is preferred. This product is commercially available as cholesteryl 12-hydroxystearate, produced by Nisshin Seiyu under the name "Sarakosu HS".

When four components, i.e., (2S,3R)-2-acetaminooctadecane-1,3-diol (A), (2S,3R)-2-octadecanoylaminoalkane-1,3-diol (B), cholesterol (C) and cholesteryl hydroxystearate (D) are used, the weight proportions of A to B, B to C and C to D preferably range from 1:1 to 2:5, from 2:1 to 1:2 and from 3:1 to 1:1, respectively.

When (2S,3R)-2-acetaminooctadecane-1,3-diol (A), (2S, 3R)-2-hexadecanoylaminoalkane-1,3-diol (B), cholesterol (C) and cholesteryl hydroxystearate (D) are mixed, the weight proportions of A to B, B to C and C to D preferably range from 1:1 to 1:3, from 2:1 to 1:2 and from 3:1 to 1:1, respectively.

Alternatively, in order to draw a phase equilibrium diagram with three poles, the components (A) and (B) may be mixed in a fixed ratio before being combined with the other components C and D.

Thus, racemic 2-acetaminoalkane-1,3-diol (A) and racemic 2-acylaminoalkane-1,3-diol (B) are mixed (A+B) in a weight proportion ranging from 1:1 to 1:2, and then combined with cholesterol (C) and cholesteryl hydroxystearate (D). Then, the weight proportion of A+B to C preferably ranges from 5:4 to 5:1, but is more preferably in the range of 3:2 to 2:1, whereas the weight proportion of C to D preferably ranges from 4:1 to 1:5, but is more preferably in the range of from 2:1 to 1:1.

For example, when (2S,3R)-2-acetaminooctadecane-1,3-diol (A) and (2S,3R)-2-octadecanoylaminooctadecane-1,3-diol (B) are mixed (A+B) in a weight proportion ranging from 1:1 to 1:2, and then combined with cholesterol (C) and cholesteryl hydroxystearate (D), the preferred proportion ranges of A+B to C and C to D are the same as described above.

The optional additive according to the invention may also be a fatty acid having a higher carbon atom content, preferably isostearic acid. Isostearic acid for use in this invention is available from Wako Pure Chemical Industry Ltd.

When (2S,3R)-2-acetaminohexadecane-1,3-diol (A), (2S, 3R)-2-(2'-hydroxyhexadecanoylamino)hexadecane-1,3-diol (B), cholesterol (C) and isostearic acid (D) are mixed, the weight proportions of A to B, B to C and C to D preferably range from 1:4 to 2:7, from 4:1 to 7:1, and from 1:1 to 1:4, respectively.

When (2S,3R)-2-acetaminooctadecane-1,3-diol (A), (2S, 3R)-2-(2'-hydroxyhexadecanoylamino)octadecane-1,3-diol (B), cholesterol (C) and isostearic acid (D) are mixed, the weight proportions of A to B, B to C and C to D preferably range from 1:1 to 1:4, from 4:1 to 1:2 and from 1:1 to 1:5, respectively.

Alternatively, racemic 2-acetaminooctadecane-1,3-diol (A) and racemic 2-(2'-hydroxyhexadecanoyl) aminooctadecane-1,3-diol (B), when mixed in a weight proportion of 1:4, form a stable liquid crystal structure together with cholesterol (C) and isostearic acid (D). The weight proportion of A+B to C preferably ranges from 5:1 to 2:1 and preferably from 5:1 to 3:1, but is more preferably around 5:1, whereas the weight proportion of C to D preferably ranges from 1:1 to 1:4, but is more preferably in the range of 1:3 to 1:4.

Also, (2S,3R)-2-acetaminooctadecane-1,3-diol (A) and (2S,3R,2'RS)-2-(2'-hydroxyhexadecanoyl) aminooctadecane-1,3-diol (B), when mixed in a weight proportion of either 1:2, 1:5 or 1:8, form a stable liquid crystal structure together with cholesterol (C) and isostearic acid (D).

In the first mixture, i.e., A:B=1:2, the preferable ratio of (A+B) to C is around 5:1, whereas that of C to D ranges from 1:1 to 1:4, but more preferably 1:1 to 1:3. In the second mixture, i.e., A:B=1:5, the preferable ratio of (A+B) to C ranges from 5:1 to 3:1, but is more preferably around 5:1, whereas that of C to D ranges from 1:1 to 1:4, but is more preferably around 1:1. In the third mixture, i.e., A:B=1:8, the preferable ratio of (A+B) to C ranges from 5:1 to 2:1 preferably from 5:1 to 3:1, whereas that of C to D ranges from 1:1 to 1:4, but is more preferably around 1:4.

Figure 5:
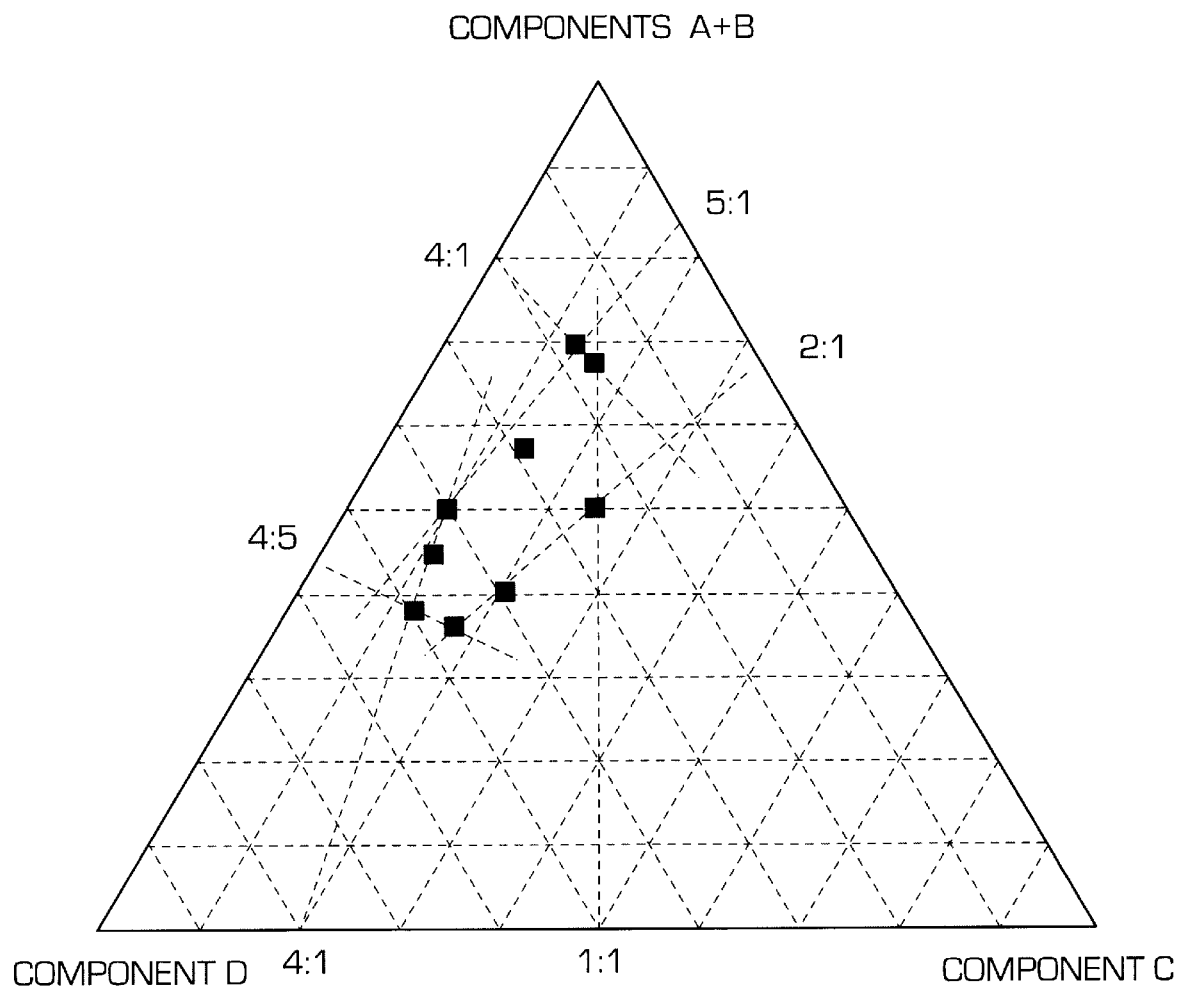
FIG. 5 shows a ternary phase equilibrium diagram consisting of (2S,3R)-2acetaminoalkane-1,3-diol and (2S,3R)-2-acylaminoalkane-1,3-diol (A+B), cholesterol (C) and isostearic acid (D)

For example, FIG. 5 also includes the phase equilibrium obtained for a mixture of (2S,3R)-2-acetaminohexadecane-1,3-diol and (2S,3R)-2-(2'-hydroxyhexadecanoylamino) octadecane-1,3-diol; cholesterol (C) and isostearic acid (D).

Preferably, a triglyceride is added to the composition of this invention. Its addition can stabilize and prolong the life of the liquid crystal or lamellar liquid crystal structure.

Typical examples of the triglyceride include commercially available glyceryl tricaprate, glyceryl tricaprilate, glyceryl trioleate, glyceryl tri-2-ethylhexanoate, etc. The addition amount of glyceride preferably ranges from 5 to 10% by weight of the composition.

Formation of the liquid crystal or lamellar liquid crystal structure can be verified by the method of Mizushima et al. described in Yukagaku, p. 656, 1994. According to this method, associative mechanism and phase behavior of the composition are observed through a polarizing microscope and analyzed through X-ray diffraction and differential scanning calorimetry.

The above-described composition may also comprise a cosmetic or pharmaceutical medium, so that it can be used as a cosmetic product, a hair-protecting product or a bath additive.

To prepare such a product, a preferred method is to first mix the aforementioned components and/or glyceride in a predetermined proportion, dissolve the mixture by heating, and cool to obtain a paste. The paste is then added to a cosmetic or pharmaceutical medium.

The cosmetic or pharmaceutical product may be prepared in the form of an emulsion such as a milky lotion, cream, shampoo, etc., or a lotion where the hydrophilic solution and the lipophilic solution are separated.

The content of the composition that is added to a cosmetic or pharmaceutical product is not particularly limited. In the case of an emulsion, the addition amount can range preferably from 0.001 to 10%, more preferably from 0.01 to 5%, still more preferably from 0.02 to 3% by weight of the product.

The emulsion can be in the form of a water phase surrounded by a lipid phase or vice versa, the lipid phase being the composition according to the invention. In this case, the lipid phase can account for 5 to 60% by weight of the total emulsion, the water phase 30 to 85% and the emulsifier 1 to 20%, preferably 2 to 12%.

Examples of the composition for use in a bath, in accordance with the invention, may include bath oil, bath salt and body shampoo.

Examples of the hair-protecting composition may include a cosmetic product for hair washing such as a shampoo, hair rinse, etc., a hair-dressing product such as a hair liquid, hair cream, hair spray, etc., and a hair restorer such as a hair tonic or other hair treatment products.

For use in baths and hair washing, there is no particular limitation on the concentration of the composition contained in the bath or hair washing product. However, it is usually from 0.01 to 10%, preferably 0.01 to 5% by weight of the total product.

The composition according to the invention can also be used for preparing a foundation, a lipstick and a skin cream, by virtue of its moisture-retaining capacity.

When the composition according to the invention is used for a cosmetic or pharmaceutical product, it gives the same effect as a known natural ceramide extracted from bovine brain.

EXAMPLES

Preparation of the Composition of the Invention

Compositions according to the invention were prepared by mixing components A, B and C, optionally together with component D, in the weight proportions indicated below. In the description below, racemic 2-acetaminoalkane-1,3-diol and its (2S,3R) isomer are represented by letter A and (2S,3R)-A, respectively, whereas racemic 2-acylaminoalkane-1,3-diol and its (2S,3R) isomer are represented by letter B and (2S,3R)-B, respectively. Component C means "cholesterol". When component D was used, it is indicated in parentheses.

Composition 1: (2S,3R)-A in which $R_1$ is $C_{15}H_{31}$:(2S, 3R)-B in which $R_1$ is $C_{15}H_{31}$ and $R_2$ is $C_{17}H_{33}CO$:C= 2:6:3. Component B used in this preparation had a purity in excess of 75%.

Composition 2: (2S,3R)-A in which $R_1$ is $C_{15}H_{31}$:(2S, 3R)-B in which $R_1$ is $C_{13}H_{27}$ and $R_2$ is $C_{17}H_{33}CO$:C= 2:5:3. Component B used in this preparation had a purity in excess of 75%.

Composition 3: (2S,3R)-A in which $R_1$ is $C_{13}H_{27}$:(2S, 3R)-B in which $R_1$ is $C_{13}H_{27}$ and $R_2$ is $C_{17}H_{33}CO$:C= 2:4:3. Component B used in this preparation had a purity in excess of 75%.

Composition 4: (2S,3R)-A in which $R_1$ is $C_{13}H_{27}$:(2S, 3R)-B in which $R_2$ is $C_{15}H_{31}$ and $R_3$ is $C_{17}H_{33}CO$:C= 1:3:2. Component B used in this preparation had a purity in excess of 75%.

Composition 5: (2S,3R)-A in which $R_1$ is $C_{15}H_{31}$:(2S, 3R)-B in which $R_1$ is $C_{15}H_{31}$ and $R_2$ is $C_{17}H_{35}CO$:C:D (cholesteryl hydroxystearate)=1:2:2:1.

Composition 6: (2S,3R)-A in which $R_1$ is $C_{13}H_{27}$:(2S, 3R)-B in which $R_1$ is $C_{15}H_{31}$ and $R_2$ is $C_{17}H_{35}CO$:C:D (cholesteryl hydroxystearate)=2:2:3:1.

Composition 7: (2S,3R)-A in which $R_1$ is $C_{13}H_{27}$:(2S, 3R)-B in which $R_1$ is $C_{13}H_{27}$ and $R_2$ is $C_{15}H_{31}CO$:C:D (cholesteryl hydroxystearate)=1:3:2:1.

Composition 8: (2S,3R)-A in which $R_1$ is $C_{15}H_{31}$:(2S, 3R)-B in which $R_1$ is $C_{15}H_{31}$ and $R_2$ is $C_{15}H_{31}CO$:C:D (cholesteryl hydroxystearate)=2:4:3:3.

Composition 9: (2S,3R)-A in which $R_1$ is $C_{13}H_{27}$:(2S, 3R)-B in which $R_1$ is $C_{17}H_{35}$ and $R_2$ is $C_{17}H_{35}CO$:C:D (cholesteryl hydroxystearate)=2:2:3:1.

Composition 10: (2S,3R)-A in which $R_1$ is $C_{15}H_{31}$:(2S, 3R)-B in which $R_1$ is $C_{17}H_{35}$ and $R_2$ is $C_{15}H_{31}CO$:C:D (cholesteryl hydroxystearate)=1:2:2:1.

Composition 11: (2S,3R)-A in which $R_1$ is $C_{15}H_{31}$:(2S, 3R)-B in which $R_1$ is $C_{11}H_{23}$ and $R_2$ is $C_{17}H_{35}CO$:C:D (cholesteryl hydroxystearate)=2:2:3:1.

Composition 12: (2S,3R)-A in which $R_1$ is $C_{13}H_{27}$:(2S, 3R)-B in which $R_1$ is $C_{13}H_{27}$ and $R_2$ is $C_{17}H_{35}CO$:C:D (cholesteryl hydroxystearate)=2:4:3:3.

Composition 13: A in which $R_1$ is $C_{15}H_{31}$:B in which $R_1$ is $C_{15}H_{31}$ and $R_2$ is $C_{14}H_{29}CH(OH)CO$=1:5. (A+B) :C:D (isostearic acid)=5:1:4.

Composition 14: A in which $R_1$ is $C_{15}H_{31}$:B in which $R_1$ is $C_{15}H_{31}$ and $R_2$ is $C_{12}H_{25}CH(OH)CO$=1:6. (A+B) :C:D (isostearic acid)=5:1:3.

Composition 15: A in which $R_1$ is $C_{13}H_{27}$:B in which $R_1$ is $C_{15}H_{31}$ and $R_2$ is $C_{14}H_{29}CH(OH)CO$=1:4. (A+B) :C:D (isostearic acid)=5:1:3.

Composition 16: A in which $R_1$ is $C_{13}H_{27}$:B in which $R_1$ is $C_{15}H_{31}$ and $R_2$ is $C_{16}H_{33}CH(OH)CO$=1:3. (A+B) :C:D (isostearic acid)=3:1:4.

Composition 17: (2S,3R)-A in which $R_1$ is $C_{15}H_{31}$:(2S,3R)-B in which $R_1$ is $C_{15}H_{31}$ and $R_2$ is $C_{14}H_{29}CH(OH)$ CO:C:D (isostearic acid)=1:4:1:4.

Composition 18: (2S,3R)-A in which $R_1$ is $C_{15}H_{31}$:(2S,3R)-B in which $R_1$ is $C_{13}H_{27}$ and $R_2$ is $C_{14}H_{29}CH(OH)$ CO:C:D (isostearic acid)=1:4:1:4.

Composition 19: (2S,3R)-A in which $R_1$ is $C_{13}H_{27}$:(2S,3R)-B in which $R_1$ is $C_{15}H_{31}$ and $R_2$ is $C_{14}H_{29}CH(OH)$ CO:C:D (isostearic acid)=1:4:1:4.

Composition 20: (2S,3R)-A in which $R_1$ is $C_{15}H_{31}$:(2S,3R)-B in which $R_1$ is $C_{15}H_{31}$ and $R_2$ is $C_{16}H_{33}CH(OH)$ CO:C:D (isostearic acid)=1:4:1:4.

Composition 21: (2S,3R)-A in which $R_1$ is $C_{13}H_{27}$:(2S,3R)-B in which $R_1$ is $C_{13}H_{27}$ and $R_2$ is $C_{14}C_{29}CH(OH)$ CO:C:D (isostearic acid)=1:4:1:3.

Composition 22: A in which $R_1$ is $C_{15}H_{31}$:B in which $R_1$ is $C_{15}H_{31}$ and $R_2$ is $C_{17}H_{35}CO=1:1$. (A+B):C:D (cholesteryl hydroxystearate)=4:3:1.

Composition 23: A in which $R_1$ is $C_{15}H_{31}$:B in which $R_1$ is $C_{15}H_{31}$ and $R_2$ is $C_{13}H_{27}CO=1:2$. (A+B):C:D (cholesteryl hydroxystearate)=3:2:1.

Composition 24: A in which $R_1$ is $C_{13}H_{27}$:B in which $R_1$ is $C_{15}H_{31}$ and $R_2$ is $C_{17}H_{35}CO=1:1$. (A+B):C:D (cholesteryl hydroxystearate)=4:3:1.

Composition 25: A in which $R_1$ is $C_{13}H_{27}$:B in which $R_1$ is $C_{15}H_{31}$ and $R_2$ is $C_{15}H_{31}CO=1:1$. (A+B):C:D (cholesteryl hydroxystearate)=4:2:1.

Observation of Lamellar Liquid Crystal Structure

The apparatus used were as follows:

Differential scanning calorimeter DSC 220, manufactured by Seiko Instrument Inc.;

Small angle X-ray scattering device PW 3050, manufactured by Philips Japan Ltd.;

Polarizing microscope, manufactured by Olympus Optical Co.;

A composition according to the invention was completely melted by heating above the melting temperature and stirred vigourously. The melted composition formed a uniform, transparent liquid. After this was observed, the liquid was allowed to stand in room temperature and further at 25° C. for one to two hours, to obtain a solid product.

About 10 mg of product were sampled in a sealable silver pan and analyzed by DSC at a heating rate of 2° C./min, in order to observe the phase transition of the composition.

On the other hand, a composition was melted at a temperature ranging from 120 to 140° C. When the melt was cooled, it generated heat at about 72° C. while maintaining the state of super-cooled liquid. It was then transformed into a liquid crystal state. The liquid crystal state was analyzed by X-ray diffraction just after the formation of liquid crystal and 15 days later. Diffraction peaks were observed at regular intervals at the low angle region: 41.8 Å (2θ=2.2°), 20.6 Å (2θ=4.3°), 13.4 Å (2θ=6.6°) and 10.2 Å (2θ=8.6°) and the peak ratio was 1:1/2:1/3:1/4. A blurred halo was also observed at 4.5 Å. These observations indicate that the structure thus obtained was a lamellar liquid crystal.

The compositions 1 to 25 were observed on a polarizing microscope to study the associated state of the phase. The phase behavior was analyzed by DSC and the structure by a small angle X-ray scattering device. The results showed that the compositions formed a lamellar liquid crystal structure.

The stability of the thus obtained lamellar liquid crystal was tested, for example, with the following compositions:

Composition 1': (2S,3R)-2-acetaminoalkane-1,3-diol (A) and (2S,3R)-2-acylaminoalkane-1,3-diol (B) mixed in a proportion ranging from 1:1 to 1:3 and component B to cholesterol (C) in a weight proportion ranging from 2:1 to 1:1.

Composition 5': (2S,3R)-2-acetaminoalkane-1,3-diol (A) and (2S,3R)-2-acylaminoalkane-1,3-diol (B) mixed in a weight proportion ranging from 1:2 to 1:1; components (A+B) and cholesterol (C) in a weight proportion ranging from 3:2 to 2:1; and component (C) and cholesteryl hydroxystearate (D) in a weight proportion ranging from 2:1 to 1:1.

Composition 17': (2S,3R)-2-acetaminoalkane-1,3-diol (A) and (2S,3R)-2-acylaminoalkane-1,3-diol (B) mixed in a weight proportion ranging from 1:2 to 1:8; components (A+B) and cholesterol (C) in a weight proportion ranging from 5:1 to 2:1; and component (C) and isostearic acid (D) in a weight proportion ranging from 1:1 to 1:4.

The product thus obtained maintained a lamellar liquid crystal structure even after 14 days without crystallizing.

However, the object of the invention is not limited to the above weight proportions. To form a desired liquid crystal structure, the components A, B, C and optionally D, may be mixed in the range defined in ternary phase equilibrium diagrams. These diagrams, shown in FIGS. 2 to 6, thus define a preferable range of the components to be added to form a liquid crystal phase.

Figure 2:
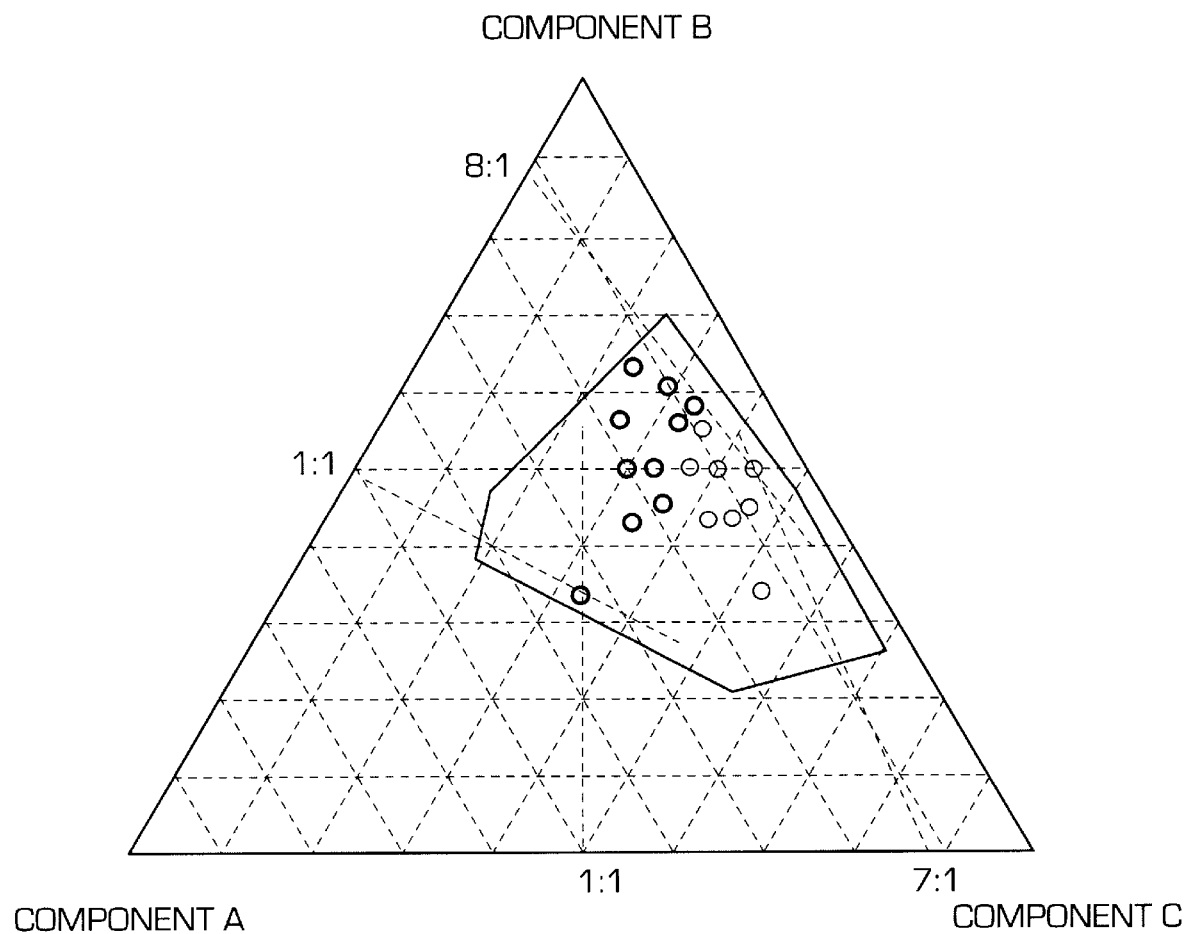
FIG. 2 shows a ternary phase equilibrium diagram consisting of (2S,3R)-2-acetaminoalkane-1,3-diol (A), (2S,3R)-2-acylaminoalkane-1,3-diol (B) and cholesterol (C)

FIG. 2 shows a ternary phase equilibrium diagram established using (2S,3R)-2-acetaminoalkane-1,3-diol (A), (2S,3R)-2-oleoylaminoalkane-1,3-diol (B) and cholesterol (C). The marks ⊚, ○ and X indicate very stable, stable and unstable lamellar liquid crystal domains, respectively.

Figure 3:
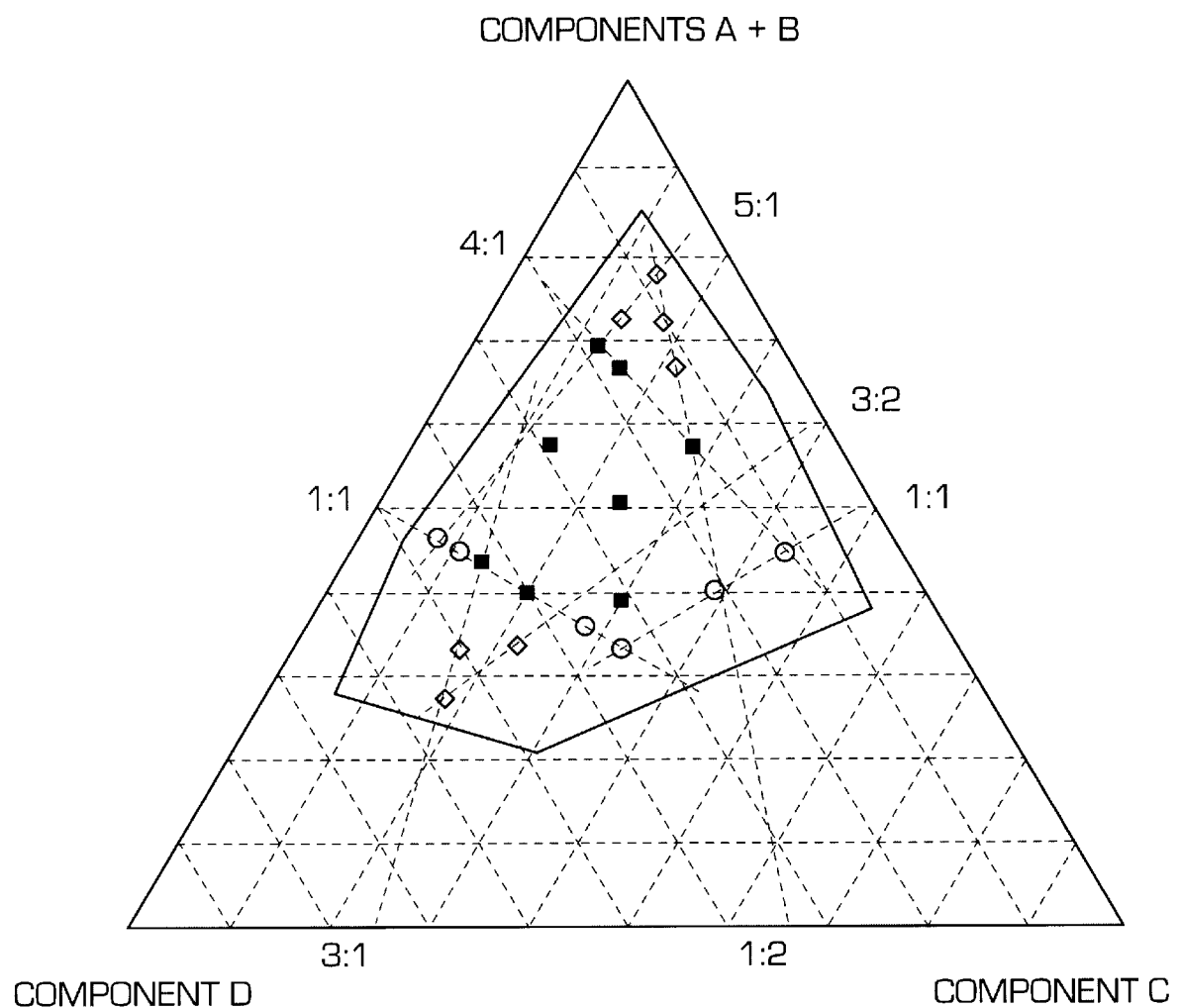
FIG. 3 shows a ternary phase equilibrium diagram consisting of (2S,3R)-2acetaminoalkane-1,3-diol and (2S,3R)-2-acylaminoalkane-1,3-diol (A+B), cholesterol (C) and cholesteryl hydroxystearate (D)

FIG. 3 shows a ternary phase equilibrium diagram established using a mixture of (2S,3R)-2-acetaminooctadecane-1,3-diol (A) and (2S,3R)-2-octadecanoylaminoalkane-1,3-diol (B), cholesterol (C) and cholesteryl hydroxystearate (D). The marks ○, □ and ■ indicate the formation of stable lamellar liquid crystal when A and B are mixed in a proportion of 1:1,1:2 and both of 1:1 and 1:2, respectively.

Figure 4:
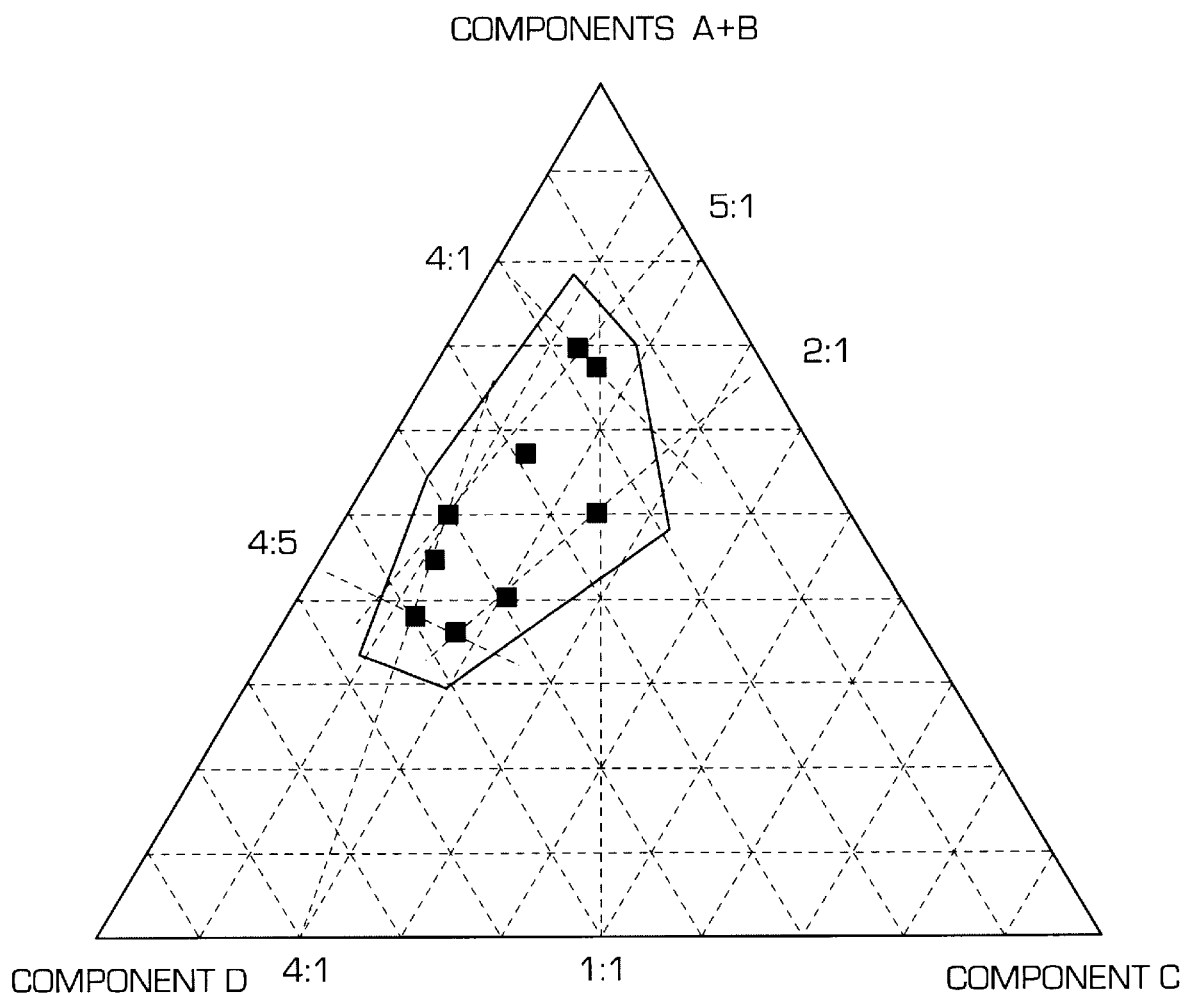
FIG. 4 shows a ternary phase equilibrium diagram consisting of 2-acetaminoalkane-1,3-diol and 2-acylaminoalkane-1,3-diol (A+B), cholesterol (C) and isostearic acid (D)

FIG. 4 shows a ternary phase equilibrium diagram established using a mixture of 2-acetaminoalkane-1,3-diol (A) and 2-acylaminoalkane-1,3-diol (B), cholesterol (C) and isostearic acid (D). The compositions that were used include Nos. 13 to 16 as described in the Examples, and the mark ■ indicates the domain of lamellar liquid crystal formation.

FIG. 5 shows a ternary phase equilibrium diagram established using a mixture of (2S,3R)-2-acetaminohexadecane-1,3-diol (A) and (2S,3R)-2-(2-hydroxyhexadecanoylmino)octadecane-1,3-diol (B), cholesterol (C) and isostearic acid (D). The compositions that were used include Nos. 17 to 21 as described in the Examples, and the mark ■ indicates the domain of lamellar liquid crystal formation.

Figure 6:
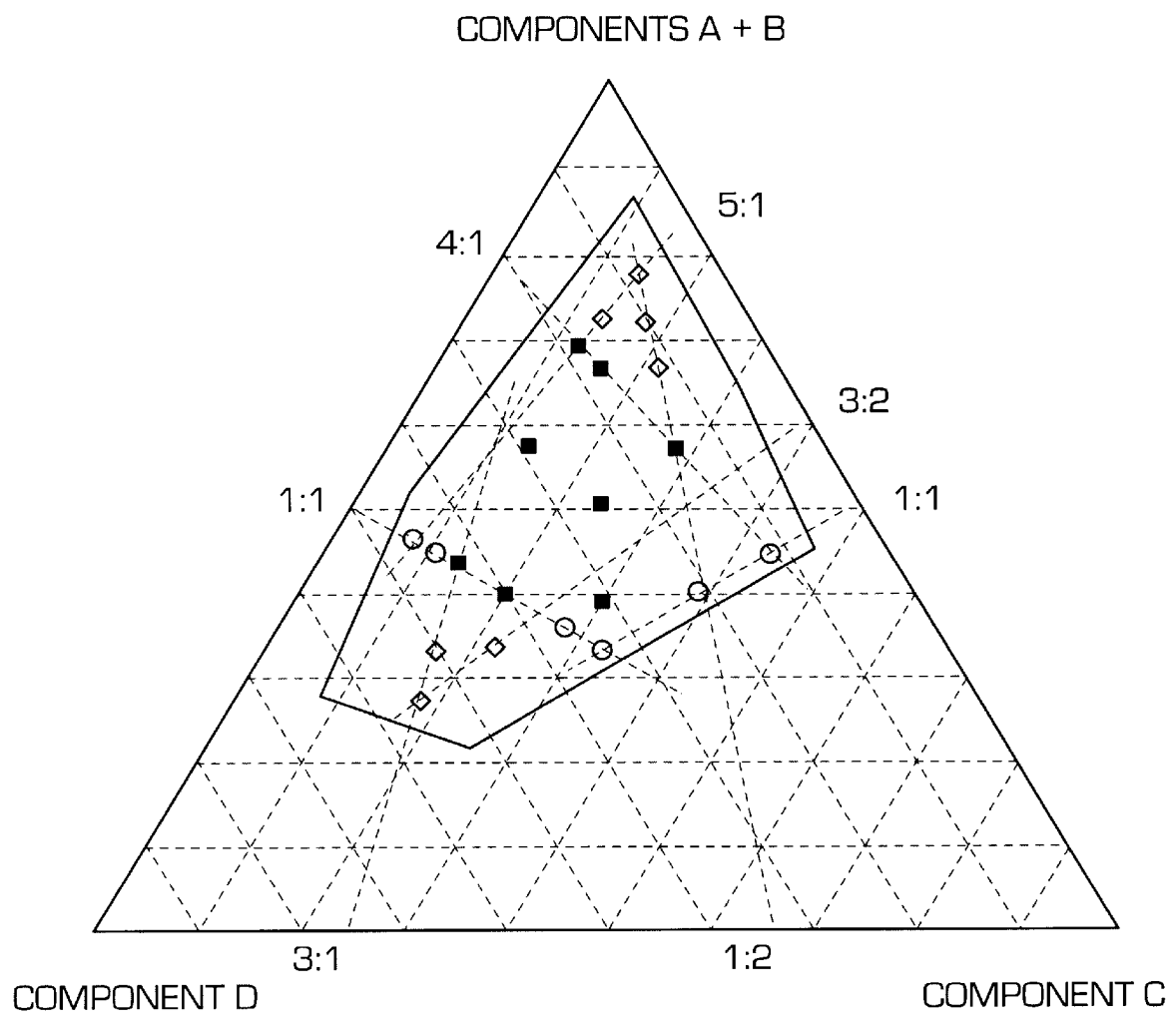
FIG. 6 shows a ternary phase equilibrium diagram consisting of 2-acetaminoalkane-1,3-diol and 2-acylaminoalkane-1,3-diol (A+B), cholesterol (C) and cholesteryl hydroxystearate (D)

FIG. 6 shows a ternary phase equilibrium diagram established using a mixture of 2-acetaminoalkane-1,3-diol (A) and 2-acylaminoalkane-1,3-diol (B), cholesterol (C) and cholesteryl hydroxystearate (D). The marks ○, □ and ■ indicate the formation of stable lamellar liquid crystal when the components A and B are mixed in a proportion of 1:1,1:2 and both of 1:1 and 1:2, respectively;

Water-Retention Test 1

Samples 1 to 4 were each prepared by mixing ingredients by weight % as indicated below. Each sample contained at least 2.0 g of purified water. The samples were allowed to stand at 37° C. and a humidity of 35+ or −2%, and the water evaporation of each sample was measured every 30 minutes.

Sample 1: 10% of composition 1, 2% Decaglyn 1-M* and 88% purified water;

Sample 2: 10% of composition 1 and 90% purified water;

Sample 3: 2% Decaglyn 1-M and 98% purified water
Sample 4: 100% purified water.
trade name of decaglyceryl monomyristate, produced by Nikko Chemical Co. Ltd.

Figure 7:
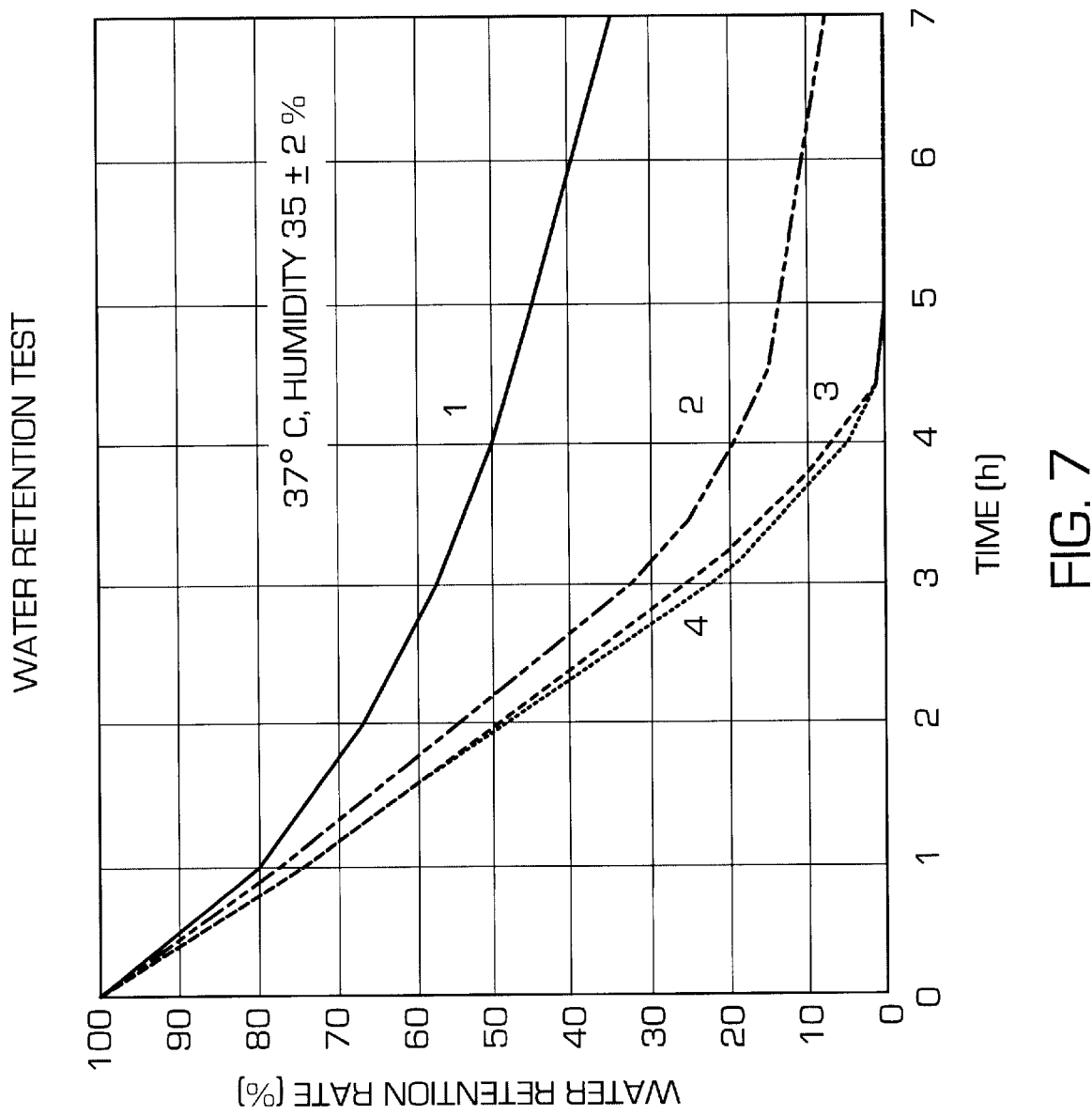
FIGS. 7 to 9 show the results of a water-retention test effected with compositions 1, 22 and 13 according to the invention, relative to corresponding blank samples not containing the composition of the invention.

The results are shown in FIG. 7, where "100% water-retention ratio" means no water loss and "0%" means total water loss. As shown in FIG. 7, in sample 3 which contained 2% Decaglyn 1-M and 98% water, the ratio became 0% after 4 to 5 hours. In comparison, in sample 2 which contained 10% of composition 1, the ratio was 8% after 7 hours. In sample 1 where composition 1 was further supplemented with 2% Decaglyn 1-M, the ratio was 35% after 7 hours.

Water-Retention Test 2

Figure 8:
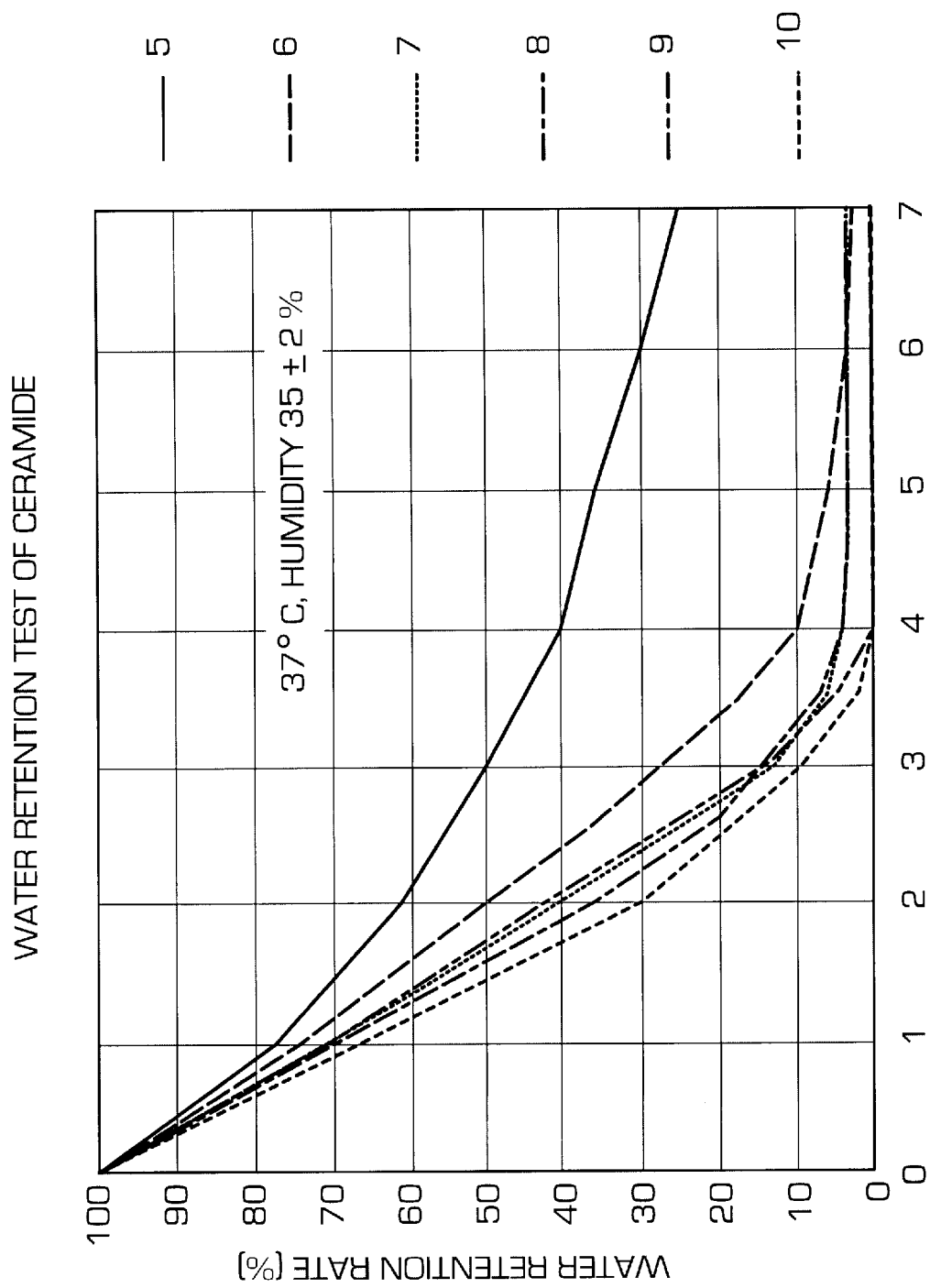

Samples 5 to 10 were prepared and tested as described in water-retention test 1:

Sample 5: 10% of composition 5, 1% Decaglyn 1-M and 89% purified water;

Sample 6: 10% of composition 5 and 90% purified water;

Sample 7: 10% glycerine, 1% Decaglyn 1-M and 89% purified water;

Sample 8: 10% glycerine and 90% purified water;

Sample 9: 1% Decaglyn 1-M and 99% purified water;

Sample 10: 100% purified water;

As seen in FIG. 8, samples 7 to 9, in which 10% glycerine and/or 1% Decaglyn 1-M were added to the purified water, exhibited a 0% water retention after 3 to 5 hours. In comparison, in sample 6 containing 10% of composition 5 of the invention, more than 6 hours passed to reach a 0% retention. Moreover, sample 5 containing 10% of composition 5 and 1% Decaglyn 1-M retained about 23% water after 7 hours of testing, and still about 15% after 10 hours.

The testing effected with compositions 17 and 22 yielded essentially the same results.

Figure 9:
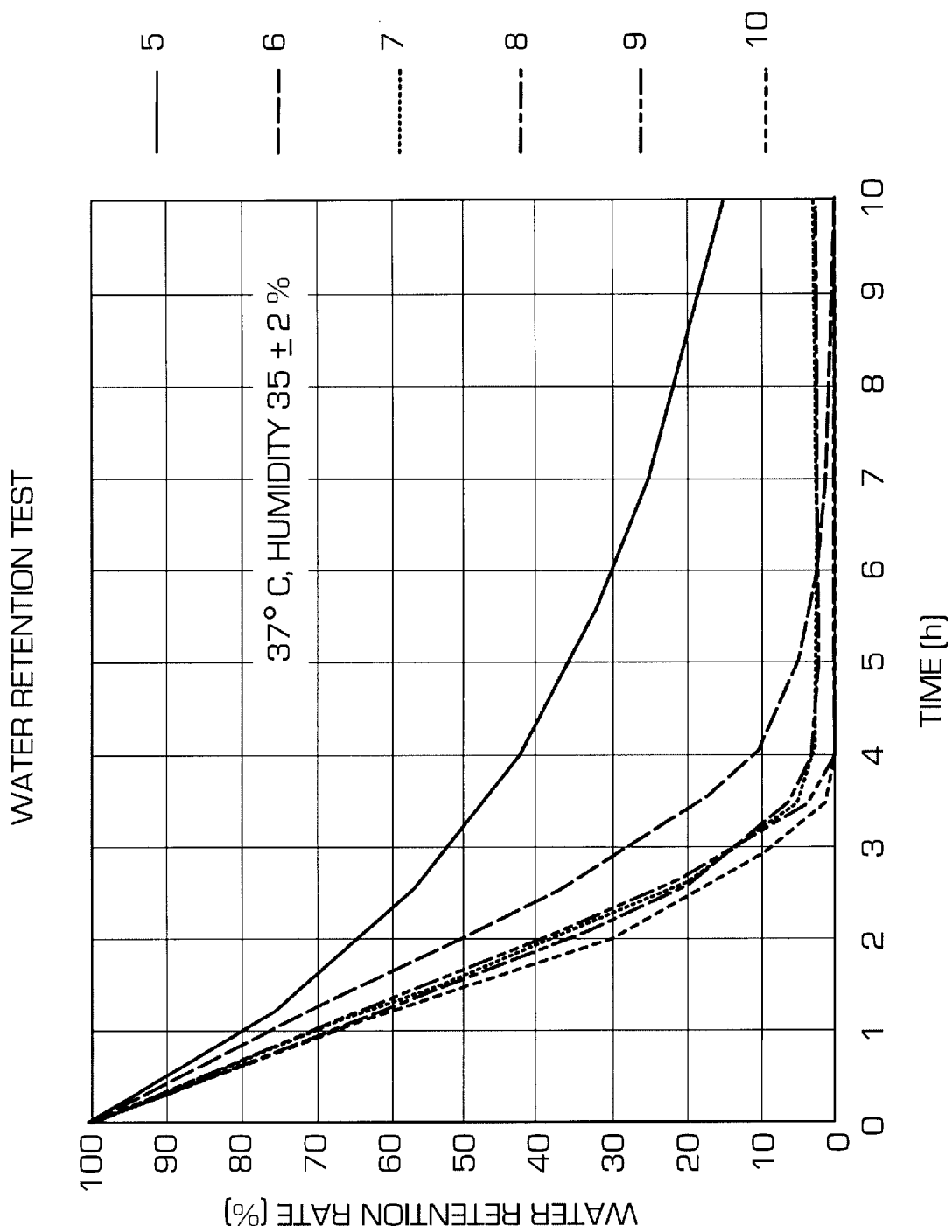

FIG. 9 shows the results that were obtained when composition 13 was used. In sample 6 containing 10% of this composition, more than 6 hours passed to reach a 0% water retention. Moreover, sample 5 which further contained 1% Decaglyn 1-M retained about 15% water after 10 hours.

Comparison between a Racemic and an Optically Active Composition

Compositions 26 and 27 were prepared from the four components indicated below, except that in composition 26 an optically active ceramide was used instead of the racemate:

| Composition 26: | |
|---|---|
| (2S,3R)-2-oleoylaminooctadecane-1,3-diol | 120 mg |
| cholesterol | 75 mg |
| palmitic acid | 75 mg |
| cholesteryl sodium sulphate | 30 mg |
| Composition 27: | |
| racemic 2-oleoylaminooctadecane-1,3-diol | 120 mg |
| cholesterol | 75 mg |
| palmitic acid | 75 mg |
| cholesteryl sodium sulphate | 30 mg |

Figure 10:
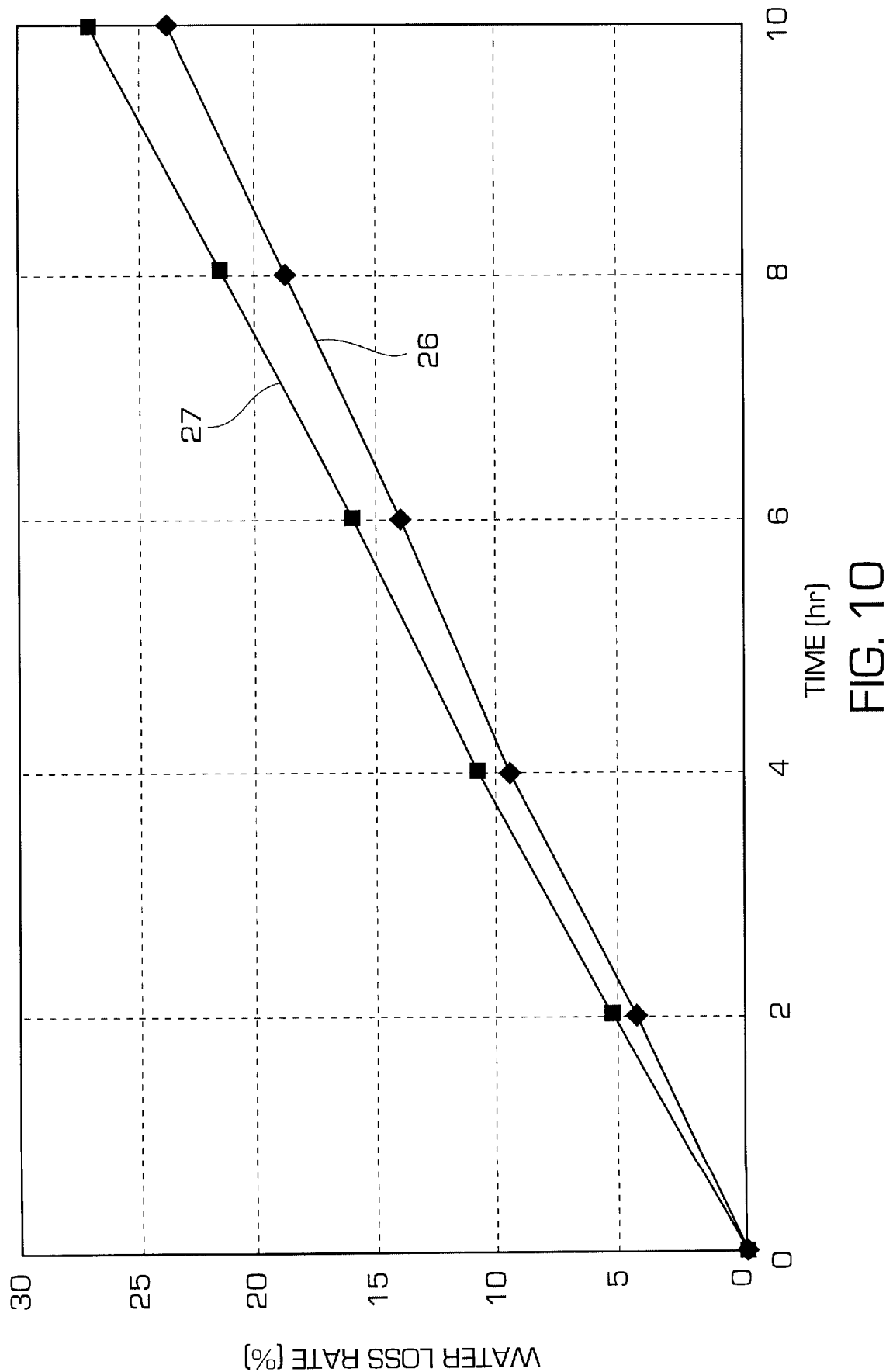
FIG. 10 shows the comparison of water-loss rate between a racemate and an optical isomer thereof, effected with compositions 26 and 27.

20 g each of compositions 26 and 27 were prepared. Ten fractions of 50 mg were sampled from each composition and placed into ten corresponding sample bottles (S-08 type). Each bottle was supplemented with 200 µl of water, annealed at 90° C. for 10 minutes and allowed to stand one night at −20° C. The procedure of annealing and freezing was repeated three times, to obtain samples 26 and 27, each including 10 bottles. The bottles were placed into an incubator at 40° C. Loss of weight (water loss) of each bottle was measured hourly over nine hours, and the average water-loss rate of the ten bottles for each sample was plotted and is shown in FIG. 10.

The water-loss rate for sample 26 was 23.6% after 10 hours and 55% after 24 hours, whereas the corresponding figures for sample 27 were 27.2% and 63%, respectively. It is therefore considered that when preparing a composition similar to intercellular lipids in stratum corneum, the (2S, 3R)-type optical isomer provides better moisture-retaining capacity than its racemate.

Likewise, compositions 28 and 29 were prepared using (2S,3R)-2-(octadecanoylamino)octadecane-1,3-diol and its racemate, instead of (2S,3R)-2-oleoylaminooctadecane-1,3-diol in composition 26 and its racemate in composition 27, respectively. Samples 28 and 29 were then prepared therefrom and tested for rate of water loss as described above. The results were substantially the same as shown in FIG. 10.

Comparison with a Pseudoceramide

Samples were prepared from the corresponding compositions described below, according to the method described in "comparison between a racemic and an optically active composition". The samples were then tested for rate of water loss. Proportions are indicated by weight.

Composition 30: (2S,3R)-2-acetaminooctadecane-1,3-diol (A):(2S,3R)-2-(cis-9-octadecenoylamino) octadecane-1,3-diol, i.e., (2S,3R)-2-oleoylaminooctadecane-1,3-diol (B): cholesterol (C)=2:6:3;

Composition 31: (2S,3R)-2-acetaminohexadecane-1,3-diol (A):(2S,3R)-2-oleoylaminooctadecane-1,3-diol (B):cholesterol (C)=2:6:3;

Composition 32: racemic 2-acetaminooctadecane-1,3-diol (A):racemic 2-oleoylaminooctadecane-1,3-diol (B):cholesterol (C)=2:6:3;

Composition 33: cholesteryl isostearate:stearic acid:cholesterol:a pseudoceramide=1:6:3:10, in which the pseudoceramide is N-(3-hexadecyloxy-2-hydroxypropyl)-N-2-hydroxyethylhexadecaamide.

Figure 11:
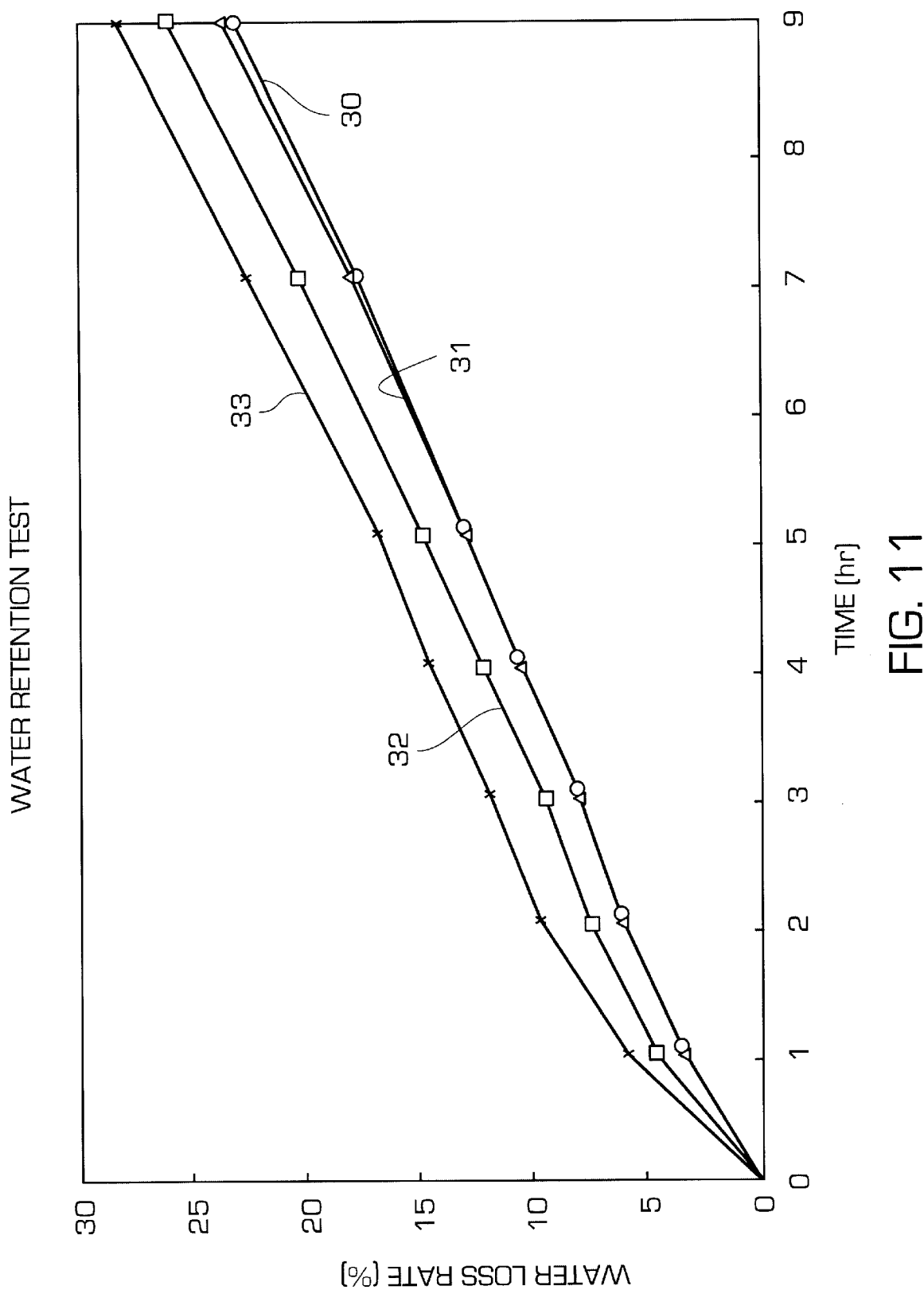
FIG. 11 shows the comparison of water loss rate between a racemate, an optical isomer and a pseudoceramide, effected with compositions 30 to 33; and, FIG. 12 shows the comparison of water loss rate between a racemate, its optical isomer and a pseudoceramide, effected using compositions 34 to 37.

FIG. 11 shows that optically active compositions 30 and 31 exhibited a better water-retention capacity than the corresponding racemic composition 32 or composition 33 comprising a pseudoceramide.

The same preparation and test were carried out using the following compositions:

Composition 34: (2S,3R)-2-acetaminooctadecane-1,3-diol (A):(2S,3R)-2-octadecanoylaminooctadecane-1,3-diol (B):cholesterol (C):cholesteryl hydroxystearate (D)=1:2:2:1;

Composition 35: (2S,3R)-2-acetaminooctadecane-1,3-diol (A):(2S,3R)-2-hexadecanoylaminohexadecane-1, 3-diol (B):cholesterol (C):cholesteryl hydroxystearate (D)=1:2:2:1;

Composition 36: racemic 2-acetaminooctadecane-1,3-diol (A):racemic 2-octadecanoylaminooctadecane-1,3-diol (B):cholesterol (C):cholesteryl hydroxystearate (D)=1:2:2:1;

Composition 37: the pseudoceramide:cholesterol:cholesteryl isostearate:stearic acid=10:3:1:6.

Figure 12:
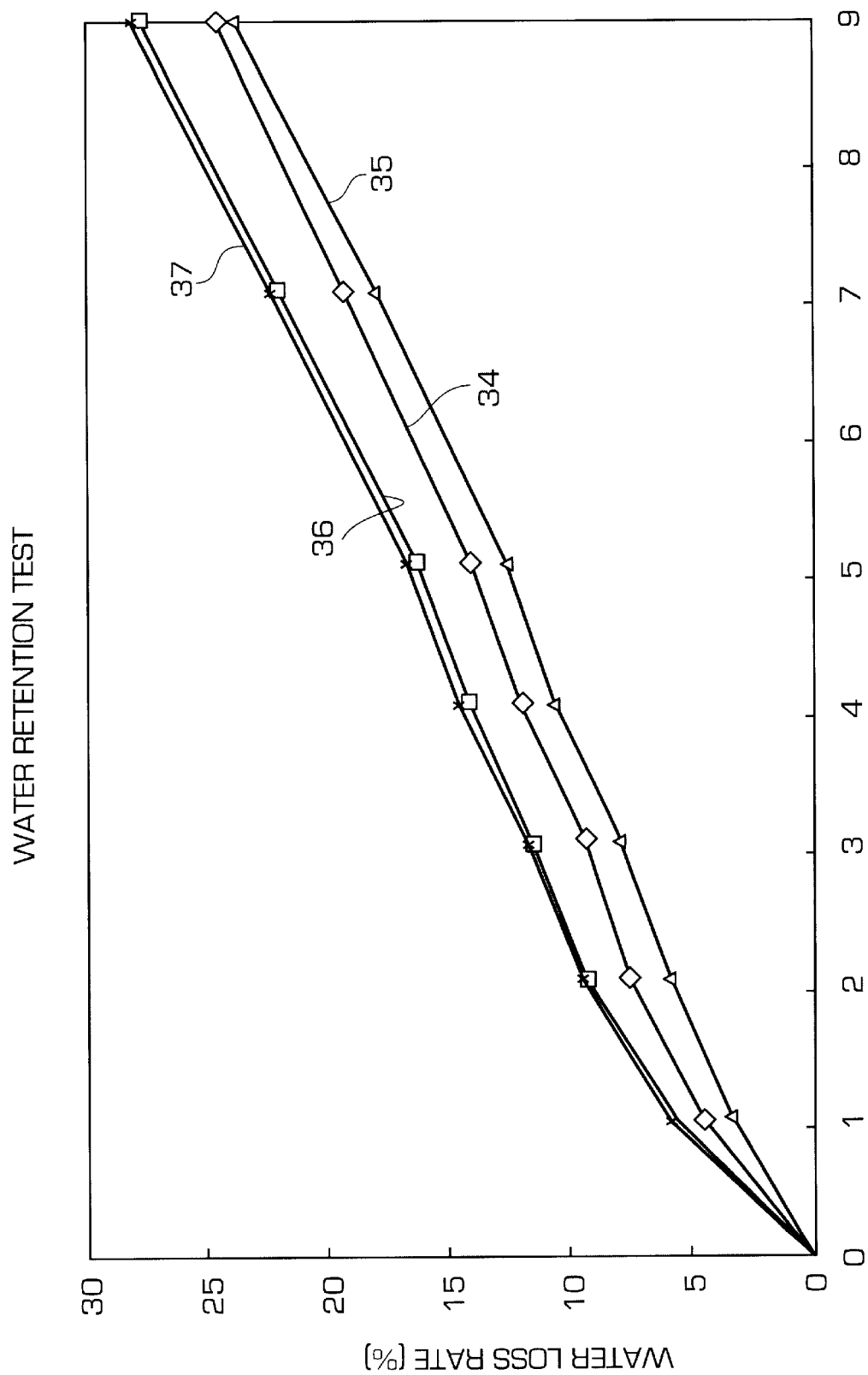

FIG. 12 shows the results that were obtained, indicating substantially the same tendency as shown in FIG. 11.

Preparation of a Cream

Cream 1

Composition 1, 5 or 17 was dissolved in a water phase consisting of purified water and propylene glycol by heating at 70° C., to obtain a hydrated liquid crystal. An oily phase was prepared by mixing the other ingredients indicated below and dissolving by heating at 70° C. The oily phase was added to the hydrated liquid crystal at 70° C. The mixture was vigourously stirred with a homogenizer, to thereby obtain a white cream having small oily micelles dispersed in the aqueous phase.

Ingredients, % by weight

| | |
|---|---|
| composition 1, 5 or 17 | 1.5 |
| α-tocopherol acetate | 0.3 |
| liquid paraffin | 5.0 |
| silicone oil | 1.0 |
| bleached beeswax | 1.0 |
| cetyl octanoate | 1.5 |
| stearic acid | 2.4 |
| cetyl alcohol | 4.0 |
| polyethyleneglycol monostearate | 1.4 |
| glyceryl monostearate | 2.4 |
| propyleneglycol | 5.0 |
| glycerine | 10.0 |
| perfume | 0.05 |
| paraben | 0.2 |
| purified water | remainder |

Cream 2

Some of the ingredients of cream 1 were replaced by the ingredients indicated below:

compositions 1, 5 or 17 in an amount of 1.5% were replaced by compositions 13 or 22 in an amount of 0.4%;

bleached beeswax in an amount of 1.0% was replaced by beeswax in an amount of 1.0%; and, propyleneglycol in an amount of 5.0% was replaced by 1,3-butyleneglycol in an amount of 5.0%.

In addition, the following ingredient was added:

glyceryl tri-(2-ethylhexanoate) in an amount of 0.02%.

Preparation of Protective Cream

To prepare a protective cream, the method described for the cream was applied mutatis mutandis.

Protective cream 1
Ingredients, % by weight

| | |
|---|---|
| composition 5 | 1.0 |
| bleached beeswax | 1.0 |
| 1,3-butylene glycol | 5.0 |
| cetyl octanoate | 1.5 |
| squalane | 30.0 |
| cetyl alcohol | 4.0 |
| polyethylene glycol monostearate | 1.4 |
| glyceryl monostearate | 2.4 |
| paraben | 0.2 |
| purified water | remainder |

Protective cream 2

Some of the ingredients of protective cream 1 were replaced by the ingredients indicated below:

composition 5 in an amount of 1.0% was replaced by composition 13 or 22 in an amount of 1.0%;

bleached beeswax in an amount of 1.0% was replaced by beeswax in an amount of 1.0%; and, paraben in an amount of 0.2% was replaced by pigment in an amount of 0.003% and glyceryl tri-(2-ethylhexanoate) in an amount of 0.06%.

Preparation of Lotion

To prepare a lotion, the method described for the cream was applied mutatis mutandis.

Lotion 1
Ingredients, % by weight

| | |
|---|---|
| composition 2, 6 or 17 | 1.5 |
| glycerine | 2.0 |
| 1,3-butylene glycol | 2.0 |
| sodium citrate | 0.1 |
| citric acid | 0.1 |
| ethanol | 5.0 |
| polyethylene oleyl ether | 0.5 |
| purified water | remainder |

Lotion 2

1.5% by weight of composition 2, 6 or 17 of lotion 1 were replaced by 0.4% by weight of composition 14 or 23.

Preparation of Milky Lotion

A water phase and an oily phase were prepared at 70° C. as described for preparing a cream. Both phases were cooled to a temperature between 40 and 50° C., combined, homogenized and emulsified. The resultant solution was cooled to 30° C. under stirring, to obtain a milky lotion.

Milky lotion 1
Ingredients, % by weight

| | |
|---|---|
| composition 3, 7 or 19 | 1.5 |
| liquid paraffin | 5.0 |
| bleached beeswax | 2.0 |
| cetyl alcohol | 0.5 |
| stearic acid | 1.5 |
| glyceryl monooleate | 1.0 |
| glyceryl monostearate | 2.4 |
| polypropylene glycol | 5.0 |
| paraben | 0.3 |
| perfume | 0.05 |
| purified water | remainder |

Milky lotion 2

Some ingredients of the milky lotion 1 were replaced by the ingredients indicated below.

compositions 3, 7 or 19 in an amount of 1.5% were replaced by composition 15 or 24 in an amount of 0.9%.

bleached beeswax in an amount of 2.0% was replaced by beeswax in an amount of 2.0%; and paraben in an amount of 0.3% was replaced by methylparaben in an amount of 0.1% and ethylparaben in an amount of 0.3%.

Preparation of Shampoo

To prepare a shampoo, the method described for the milky lotion was applied mutatis mutandis.

Shampoo 1
Ingredients, % by weight

| | |
|---|---|
| composition 4, 8 or 18 | 1.5 |
| triethylamine lauryl sulphate | 18.5 |
| 1% aqueous solution of hydroxypropylmethyl cellulose | 15.0 |
| ammonium lauryl sulphate | 8.0 |
| 1,3-dimethylol-5,5-dimethyl hydantoin | 0.15 |
| disodium ethylenediamine tetraacetate | 0.05 |
| citric acid | trace |
| sodium chloride | trace |
| perfume | 0.85 |
| purified water | remainder |

Shampoo 2

The composition of shampoo 1 was replaced by the composition indicated below:

compositions 4, 8 or 18 in an amount of 1.5% were replaced by compositions 13 or 22 in an amount of 0.4%.

In addition, the following ingredients were added:

| | |
|---|---|
| decanoic acid | 0.05% |
| cocamide | 4.0% |
| palmitic acid | 0.3% |
| glyceryl tri-(2-ethylhexanoate) | 0.02% |

Preparation of Hair-treatment Lotion

To prepare a hair-treatment lotion, the method described for the milky lotion was applied mutatis mutandis.

Hair-treatment lotion 1

Ingredients, % by weight

| | |
|---|---|
| composition 1, 10 or 18 | 0.5 |
| hydroxyethyl cellulose | 0.4 |
| ethanol | 25.0 |
| glyceryl monooleate | 2.0 |
| paraben | 0.2 |
| perfume | 0.1 |
| purified water | remainder |

Hair-treatment lotion 2

1.5% by weight of composition 1, 10 or 18 of hair-treatment lotion 1 were replaced by 0.9% by weight of composition 14 or 23.

Preparation of Lipstick

To prepare a lipstick, the method described for the milky lotion and a manufacturing method well known to those of ordinary skill were applied mutatis mutandis.

Lipstick 1

Ingredients, % by weight

| | |
|---|---|
| composition 5 | 0.5 |
| liquid lanoline | 18.0 |
| paraffin | 15.0 |
| titanium mica | 10.0 |
| glyceryl tri-(caprate, caprylate) | 12.0 |
| paraben | 0.1 |
| organic pigment | 8.0 |
| castor oil | remainder |

Lipstick 2

Some ingredients of lipstick 1 were replaced by the ingredients indicated below:

composition 5 in an amount of 0.5% was replaced by compositions 13 or 22 in an amount of 0.5%;

glyceryl tri-(caprylate, caprate) in an amount of 12.0% was replaced by glyceryl tricaprate in an amount of 6.0% and glyceryl tricaprylate in an amount of 6.0%;

castor oil (remainder) was replaced by ricin oil (remainder).

Evaluation by Users 1

The products described below were prepared with and without (blank) the composition according to the invention and tested by 20 panellists. As for the cream, lotion and milky lotion, these products were applied on the skin of the upper arm. The panellists then compared the products and corresponding blank samples with respect to spreadability, affinity and moist and tender feeling to the skin. As for the shampoo and hair-treatment lotion, hair-wiriness and wet tenderness after hair washing were compared between the products and corresponding blank samples. The results of the evaluation are shown by the number of panellists consisting of 20 persons who responded positively to the product as compared to the blank sample.

| Type of product | Evaluation |
|---|---|
| cream (composition 1) | 19/20 |
| lotion (composition 2) | 18/20 |
| milky lotion (composition 3) | 18/20 |
| shampoo (composition 4) | 17/20 |
| hair-treatment lotion (composition 1) | 18/20 |

Evaluation by Users 2

The products described below were prepared with and without (blank) the composition according to the invention and tested by panellist group A consisting of 20 female monitors aged 23 to 35, having healthy skin, and by panellist group B consisting of 20 female monitors aged 33 to 48, perceiving dry, damaged or wrinkled skin. The test was carried out in the relatively dry season covering November to December. To test the cream, protective cream, lotion, milky lotion and lipstick, the monitors previously took a bath and washed their face. Then, without using other cosmetics, the products according to the invention were applied to the right-half of the face and the inside portion of the right upper arm, whereas the blank products were applied to the left-half of the face and the inside portion of the left upper arm. The products and blank products were applied once to three times a day for 20 consecutive days.

To test the shampoo and hair-treatment lotion, monitors previously washed their hair with soap. Then, without using other hair-cosmetics, the products according to the invention were applied to the right-half of the scalp, whereas the blank products were applied to the left-half of the scalp. The products and blank products were applied once or twice a day for 20 consecutive days. The evaluation criteria were the same as those for "Evaluation by Users 1".

| | EVALUATION | |
|---|---|---|
| Type of product | Group A | Group B |
| cream (composition 5) | 15/20 | 18/20 |
| protective cream (composition 5) | 16/20 | 17/20 |
| lotion (composition 6) | 17/20 | 16/20 |
| milky lotion (composition 7) | 14/20 | 17/20 |
| shampoo (composition 8) | 14/20 | 16/20 |
| hair-treatment lotion (composition 10) | 17/20 | 18/20 |
| lipstick (composition 1) | 13/20 | 15/20 |

Evaluation by Users 3

In "Evaluation by Users 2", the compositions 5, 5, 6, 7, 8, 10 and 1 were replaced by compositions 13, 13, 14, 15, 13, 14 and 13 respectively, so that corresponding types of products were obtained. The products were then evaluated in the same way as described in "Evaluation by Users 2".

The evaluation results obtained were substantially the same as those of "Evaluation by Users 2".

Evaluation by Users 4

In "Evaluation by Users 2", the compositions 5, 5, 6, 7, 8, 10 and 1 were replaced by compositions 22, 22, 23, 24, 22, 23 and 22 respectively, so that corresponding types of products were obtained. The products were then evaluated in the same way as described in "Evaluation by Users 2".

The evaluation results obtained were substantially the same as those of "Evaluation by Users 2".

While the invention has been described in detail and with reference to specific embodiments thereof, it will be apparent to one skilled in the art that various changes and modifications can be made therein without departing from the spirit and scope thereof.

What is claimed is:
1. A composition comprising:
at least a component A selected from the group consisting of 2-acetaminoalkane-1,3-diols having the formula (I) which is in racemic form or in the form of a mixture of optically active forms:

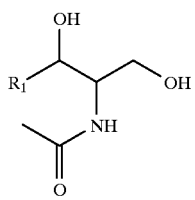

(I)

wherein $R_1$ represents a linear alkyl group having from 9 to 17 carbon atoms;
at least a component B selected from the group consisting of 2-acylaminoalkane-1,3-diols having the formula (II) which is in racemic form or in the form of a mixture of optically active forms:

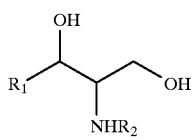

(II)

wherein $R_1$ has the same meaning as given above for formula (I) and $R_2$ represents a substituted or unsubstituted linear acyl group having from 14 to 24 carbon atoms; and
at least a component C having a sterol group, which component C having a sterol group is selected from the group consisting of cholesterol, coprostanol, stigmasterol, β-sitosterol and ergosterol.

2. The composition according to claim 1, wherein the linear acyl group represented by $R_2$ in formula (II) contains a carbon-carbon double bond.

3. The composition according to claim 1, wherein the linear acyl group represented by $R_2$ in formula (II) is unsubstituted.

4. The composition according to claim 1, wherein the linear acyl group represented by $R_2$ in formula (II) is substituted by at least one of a methyl group and a hydroxy group.

5. The composition according to claim 1, wherein component C comprises cholesterol.

6. The composition according to claim 1, wherein said components A and B are mixed in a weight proportion ranging from 1:1 to 1:8.

7. The composition according to claim 1, wherein said component A is a (2S,3R)-2-acetaminoalkane-1,3-diol having the formula (III):

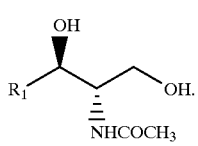

(III)

8. The composition according to claim 1, wherein said component B is a (2S,3R)-2-acylaminoalkane-1,3-diol having the formula (IV):

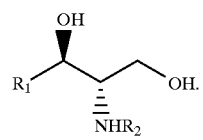

(IV)

9. The composition according to claim 7, wherein said component B is a (2S,3R)-2-acylaminoalkane-1,3-diol having the formula (IV):

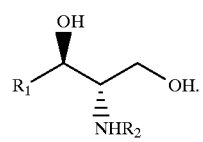

(IV)

10. The composition according to claim 1, wherein $R_2$ in component B is an acyl group having a hydroxy group at the 2-carbon position of the acyl group.

11. The composition according to claim 9, wherein $R_2$ in component B is an acyl group having a hydroxy group at the 2-carbon position of the acyl group.

12. The composition according to claim 1, wherein $R_2$ in component B is an oleoyl group.

13. The composition according to claim 9, wherein $R_2$ in component B is an oleoyl group.

14. The composition according to claim 12, wherein the weight proportion of said components A to B, said components B to C and said components A to C ranges from 1:1 to 1:8, from 7:1 to 1:3 and from 2:1 to 1:7, respectively.

15. The composition according to claim 12, wherein the weight proportion of said components A to B, said components B to C and said components A to C ranges from 1:1 to 1:8, from 7:1 to 1:1 and from 1:1 to 1:3, respectively.

16. The composition according to claim 1, which further comprises at least a component D cholesteryl hydroxystearate, isostearic acid, cholesteryl oleate, cholesteryl stearate, cholesteryl isostearate, tetradecanoic acid, hexadecanoic acid, octadecanoic acid and hydroxyoctadecanoic acid.

17. The composition according to claim 9, which further comprises at least a component D cholesteryl hydroxystearate, isostearic acid, cholesterol oleate, cholesterol stearate, cholesteryl isostearate, tetradecanoic acid, hexadecanoic acid, octadecanoic acid and hydroxyoctadecanoic acid.

18. The composition according to claim 16, wherein said component D comprises cholesteryl hydroxystearate.

19. The composition according to claim 17, wherein said component D comprises cholesteryl hydroxystearate.

20. The composition according to claim 18, wherein the total of said components A and B, said cholesterol as component C and said cholesteryl hydroxystearate as component D are mixed in a weight proportion (A+B) to C ranging from 5:4 to 5:1 and in a weight proportion C to D ranging from 4:1 to 1:5.

21. The composition according to claim 16, wherein said component D comprises isostearic acid.

22. The composition according to claim 17, wherein said component D comprises isostearic acid.

23. The composition according to claim 21, wherein component C comprises cholesterol, and wherein the total of said components A and B, said cholesterol as component C and said isostearic acid as component D are mixed in a weight proportion (A+B) to C ranging from 5:1 to 2:1 and in a weight proportion C to D ranging from 1:1 to 1:4.

24. The composition according to claim 1, which further comprises at least one compound selected from the group consisting of a triglyceride and a phospholipid.

25. The composition according to claim 9, which further comprises at least one compound selected from the group consisting of a triglyceride and a phospholipid.

26. The composition according to claim 16, which further comprises at least one compound selected from the group consisting of a triglyceride and a phospholipid.

27. The composition according to claim 17, which further comprises at least one compound selected from the group consisting of a triglyceride and a phospholipid.

28. A cosmetic product comprising the composition according to claim 1 and a cosmetically acceptable medium.

29. A cosmetic product comprising the composition according to claim 9 and a cosmetically acceptable medium.

30. A skin-protecting agent comprising the composition according to claim 1 and a cosmetically acceptable medium.

31. A skin-protecting agent comprising the composition according to claim 9 and a cosmetically acceptable medium.

32. A bath-additive agent comprising the composition according to claim 1 and a cosmetically acceptable medium.

33. A bath-additive agent comprising the composition according to claim 9 and a cosmetically acceptable medium.

34. A hair-protecting agent comprising the composition according to claim 1 and a cosmetically acceptable medium.

35. A hair-protecting agent comprising the composition according to claim 9 and a cosmetically acceptable medium.

36. A pharmaceutical product haircare comprising the composition according to claim 1 and a pharmaceutically acceptable medium.

37. A pharmaceutical product haircare comprising the composition according to claim 9 and a pharmaceutically acceptable medium.

38. A skin-protecting medicine comprising the composition according to claim 1 and a pharmaceutically acceptable medium.

39. A skin-protecting medicine comprising the composition according to claim 9 and a pharmaceutically acceptable medium.

* * * * *